(12) United States Patent
Lao et al.

(10) Patent No.: US 9,365,559 B2
(45) Date of Patent: Jun. 14, 2016

(54) CRYSTAL FORM OF DABRAFENIB AND PREPARATION METHOD OF USE THEREOF

(71) Applicant: Hangzhou Pushai Pharmaceutical Technology Co., LTD., Hangzhou (CN)

(72) Inventors: Haiping Lao, Hangzhou (CN); Xiaoxia Sheng, Hangzhou (CN); Xiaohong Sheng, Hangzhou (CN)

(73) Assignee: HANGZHOU PUSHAI PHARMACEUTICAL TECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 14/794,073

(22) Filed: Jul. 8, 2015

(65) Prior Publication Data

US 2015/0307484 A1  Oct. 29, 2015

Related U.S. Application Data

(63) Continuation of application No. PCT/CN2014/074883, filed on Apr. 8, 2014.

(30) Foreign Application Priority Data

Apr. 17, 2013 (CN) .......................... 2013 1 0134894

(51) Int. Cl.
 *C07D 417/04* (2006.01)
(52) U.S. Cl.
 CPC ........... *C07D 417/04* (2013.01); *C07B 2200/13* (2013.01)

(58) Field of Classification Search
 CPC .......................... C07B 2200/13; C07D 417/04
 See application file for complete search history.

(56) References Cited

U.S. PATENT DOCUMENTS

| 7,994,185 B2 * | 8/2011 | Rheault ................ C07D 413/04 514/275 |
| 2012/0196886 A1 | 8/2012 | Dumble et al. |
| 2014/0018372 A1 * | 1/2014 | Maier ................ A61K 31/4045 514/256 |

FOREIGN PATENT DOCUMENTS

| CN | 102083312 A | 6/2011 |
| WO | WO 2009/137391 A2 * | 11/2009 |
| WO | WO 2012/148588 A2 * | 11/2012 |

OTHER PUBLICATIONS

International Search Report and Written Opinion for International Application No. PCT/CN2014/074883, ISA, China, mailed on Jul. 8, 2014.

\* cited by examiner

*Primary Examiner* — Valerie Rodriguez-Garcia
(74) *Attorney, Agent, or Firm* — Sterne, Kessler, Goldstein & Fox P.L.L.C.

(57) ABSTRACT

The invention relates to Crystal Hydrate Form VI of Dabrafenib and preparation method thereof, wherein Crystal Hydrate Form VI of Dabrafenib has the advantage of being more stable at room temperature or in aqueous systems, and has low hygroscopicity, and thus is more suitable for a wet granulation process or being prepared into a suspension; and the present invention also relates to a pharmaceutical composition and formulations comprising Crystal Hydrate Form VI of Dabrafenib, and their use in the treatment of Raf family kinase-related diseases.

15 Claims, 15 Drawing Sheets

CRYSTAL FORM OF DABRAFENIB AND PREPARATION METHOD OF USE THEREOF

FIELD OF THE INVENTION

The present Invention relates to the crystalline forms of a drug compound. To be specific, it relates to the new crystal forms of a benzene sulfonamide thiazole compound, dabrafenib, methods of preparation and use thereof.

BACKGROUND OF THE INVENTION

Polymorphism is the ability of a solid material to exist in more than one form or crystal structure. Polymorphism may result from different molecular packing and/or molecular conformations of the molecules of a given compound in the crystal lattice. Polymorphic forms of a given compound have different physical properties, such as solubility, stability, thermal property, morphology of crystals, and mechanical property, etc. One or combination of multiple characterization methods may be used to differentiate the different crystal forms of the same compound, such as X-ray powder diffraction, differential scanning calorimetry, infrared spectroscopy, raman spectroscopy, and solid-state NMR spectroscopy, etc.

New crystalline forms (including anhydrous forms, hydrates and solvates) of the active pharmaceutical ingredients may offer better properties, such as solubility and bioavailability, stability, processability, purification ability. Some new crystalline form may serve as an intermediate crystal form to facilitate solid state transformation to a desired form. Desired new polymorphs can help formulation scientists broaden the choice of crystal forms to optimize the dosage forms.

Dabrafenib is a benzene sulfonamide thiazole compound and is a selective BRAF inhibitor. Results of the Phase I/II clinical trials show Dabrafenib has therapeutical activities and an acceptable safety profile in patients with BRAFV600E-mutan melanoma. The chemical name of Dabrafenib is N-[3-[5-(2-aminopyrimidin-4-yl)-2-(tert-butyl) thiazo-4-lyl]-2-fluoro phenyl]-2,6-difluorobenzenesulfonamide; molecular formula: $C_{23}H_{20}F_3N_5O_2S_2$; formula weight: 519.6; and chemical structural formula as follows:

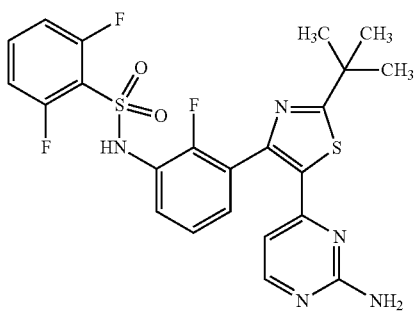 [SMILES: CC(C)(C)c1nc(-c2cccc(NS(=O)(=O)c3c(F)cccc3F)c2F)c(-c2ccnc(N)n2)s1]

Patent documents WO2009/137391A2 and U.S. Pat. No. 7,994,185B2 (incorporated into the present application by reference) disclosed identification, preparing process and uses of Dabrafenib. To be specific, example 58a~c disclosed a number of crystal forms of Dabrafenib and their preparation methods. Wherein, example 58a disclosed a crystal form (hereinafter referred to as the Known Crystal Form 1) and its preparation method. Example 58b and 58c disclosed another crystal form (hereinafter referred to as the Known Crystal Form 2) and its preparation method. Moreover, such patent documents also disclosed that Dabrafenib has the inhibitory effection on one or more Raf-family kinases. The above patent documents mentioned that the Known Crystal Form 1 is crystalline and provided its $^1$H-NMR data, XRPD pattern and DSC thermogram; the Known Crystal Form 2 was characterized by Raman, XRPD and DSC/TGA analyses to show it is different from the Known Crystal Form 1, but detailed data was not given. The above patent documents did not mention the stability and the conversion relationship of these two crystal forms.

In addition, patent documents WO2012/148588A2 (incorporated into the present application by reference) disclosed a number of crystal forms of Dabrafenib and their preparation methods. Wherein, example 1 disclosed a crystal form (hereinafter referred to as the Known Crystal Form 3) and its preparation method. Furthermore, this patent document provided further characteristic data for the Known Crystal Form 1 and the Known Crystal Form 2 which were previously mentioned in WO2009/137391A2; This patent document provided Raman, XRPD and DSC/TGA analysis data of the Known Crystal Form 1, the Known Crystal Form 2 and the Known Crystal Form 3, but it did not mention the stability and the conversion relationship of these three crystal forms.

Patent document US2012/0196886A1 disclosed a pharmaceutical composition containing Dabrafenib methanesulfonate and use thereof.

In the present research, it was discovered that the Known Crystal Form 1 has the following defects: as an anhydrate, it has about 1.9% of weight change between 20~80% RH, indicating some hygroscopicity; and it readily converts to other form(s) in water or other water containing system(s), thus unable to maintain its original form.

In the present research, it was discovered that the Known Crystal Form 2 has the following defects: it is unstable; it would convert to other form(s) when exposed to water or other water containing system(s), thus unable to maintain the original form; and after stirring in dichloromethane followed by filtering and drying, it can convert to the Known Crystal Form 1.

In the present research, it was discovered that the Known Crystal Form 3 has the following defects: It is very unstable; it can convert to the Known Crystal Form 1 at room temperature; and it may convert to other form(s) in water or other water containing system(s), thus unable to maintain the original form.

Therefore, there is a need to discover new crystal forms of Dabrafenib with good purity, improved thermodynamical stability at room temperature or in water, and/or little mass change under high humidity conditions, etc., to meet the strict demands for crystal properties in industrial production of pharmaceutical formulations.

SUMMARY OF THE INVENTION

In view of the defects in the prior art, the purpose of the present invention is mainly to provide new crystal forms of Dabrafenib with improved thermodynamical stability at room temperature or in aqueous system, and to provide preparation methods and uses thereof.

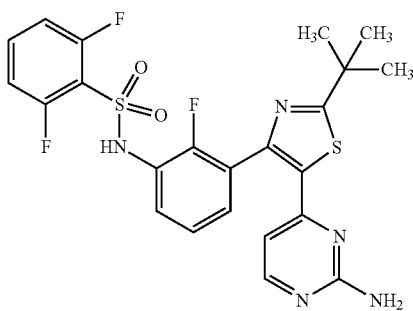 [SMILES: CC(C)(C)c1nc(-c2cccc(NS(=O)(=O)c3c(F)cccc3F)c2F)c(-c2ccnc(N)n2)s1]

Dabrafenib

According to the purpose of the present invention, Crystal Form VI of Dabrafenib (hereinafter referred to as Crystal Form VI) is provided. Crystal Form VI is an hydrate, wherein per mol of Dabrafenib contains about 1 mol of water.

Measured using Cu—Kα radiation, Crystal Form VI is characterized by a X-ray powder diffraction pattern having the specific peaks at the diffraction angle 2θ of 10.4±0.2°, 17.6±0.2°, 21.6±0.2° and 25.1±0.2°.

In one preferred embodiment of the present invention, Crystal Form VI is characterized by a X-ray powder diffraction pattern having the specific peaks at the diffraction angle 2θ of 10.4±0.2°, 11.2±0.2°, 13.1±0.2°, 13.3±0.2°, 16.7±0.2°, 17.6±0.2°, 18.3±0.2°, 21.2±0.2°, 21.6±0.2°, 25.1±0.2°, 25.8±0.2°, 27.6±0.2° and 31.8±0.2°.

In the further preferred embodiment of the present invention, Crystal Form VI is characterized by a X-ray powder diffraction pattern having the specific peaks at the diffraction angle 2θ of 8.1±0.2°, 10.4±0.2° 11.2±0.2°, 13.1±0.2°, 13.3±0.2°, 14.4±0.2°, 16.2±0.2°, 16.7±0.2°, 17.6±0.2°, 18.3±0.2°, 21.2±0.2°, 21.6±0.2°, 25.1±0.2°, 25.8±0.2°, 26.3±0.2°, 26.8±0.2°, 27.6±0.2°, 31.1±0.2°, 31.8±0.2° and 32.9±0.2°.

In the even further preferred embodiment of the present invention, Crystal Form VI is characterized by a X-ray powder diffraction pattern having the following specific peaks at the diffraction angle 2θ and their relative intensities:

| Diffraction angle 2θ | Relative intensity % |
|---|---|
| 8.1 ± 0.2° | 11.0 |
| 10.4 ± 0.2° | 40.5 |
| 11.2 ± 0.2° | 17.1 |
| 13.1 ± 0.2° | 13.2 |
| 13.3 ± 0.2° | 25.4 |
| 14.4 ± 0.2° | 10.2 |
| 16.2 ± 0.2° | 12.8 |
| 16.7 ± 0.2° | 27.6 |
| 17.6 ± 0.2° | 44.7 |
| 18.3 ± 0.2° | 13.3 |
| 21.2 ± 0.2° | 18.2 |
| 21.6 ± 0.2° | 100.0 |
| 25.1 ± 0.2° | 34.0 |
| 25.8 ± 0.2° | 16.6 |
| 26.3 ± 0.2° | 10.6 |
| 26.8 ± 0.2° | 10.0 |
| 27.6 ± 0.2° | 13.3 |
| 31.1 ± 0.2° | 12.3 |
| 31.8 ± 0.2° | 23.2 |
| 32.9 ± 0.2° | 10.3. |

Non-restrictively, in one specific embodiment of the present invention, the X-ray powder diffraction pattern of Crystal Form VI is shown in FIG. 1.

Crystal Form VI may be prepared by any one of the following preparation methods:

(1) Putting a known crystal form or an amorphous form of Dabrafenib into a solvent system to form a suspension, stirring to recrystallize, separating and drying the precipitated crystals to get Crystal Form VI of Dabrafenib, wherein the solvent system is selected from water or a mixed solvents of water and an organic solvent, and the organic solvent is selected from $C_1$~$C_4$ alcohols, $C_4$~$C_5$ ester, $C_2$~$C_5$ ethers, $C_3$~$C_4$ ketones, tetrahydrofuran, nitromethane, acetonitrile, $C_5$~$C_8$ alkanes and their mixtures;

Preferably, the known crystal form of Dabrafenib is the Known Crystal Form 2 of Dabrafenib;

Preferably, the organic solvent is selected from methanol, ethanol, propanol, butanol, ethyl acetate, isopropyl acetate, ethyl ether, methyl tert-butyl ether, acetone, butanone, tetrahydrofuran, nitromethane, acetonitrile, methyl cyclohexane, n-heptane, n-hexane or cyclohexane;

Preferably, the volume content of water in the mixed solvents of water and organic solvents is at least 0.01%, and more preferably, at least 0.1%;

Preferably, the amount of the known crystal form or the amorphous form of Dabrafenib is 1.1~20 times of its solubility in the solvent system at the operation temperature, and more preferably, 1.5~10 times;

Preferably, the operation temperature is room temperature to 60° C., and more preferably, room temperature;

Preferably, the duration of recrystallization is 3~14 days, and more preferably, 3~7 days.

(2) At room temperature, forming a solution of a known crystal form or an amorphous form of Dabrafenib by completely dissolving them in a mixed solvent of water and an organic solvent, placing the solution in a sealed atmosphere full of the diffusive solvent to precipitate crystals, separating and drying the precipitated crystal to get Crystal Form VI of Dabrafenib, wherein the organic solvent is selected from nitromethane or isopropyl alcohol and the diffusive solvent is the volatile ether;

Preferably, the known crystal form of Dabrafenib is the Known Crystal Form 2 of Dabrafenib;

Preferably, the volume content of water in the mixed solvent of water and organic solvent is at least 0.01%~10%, and more preferably, at least 0.1%~10%;

Preferably, the diffusive solvent is mineral ether or isopropyl ether;

Preferably, the solution concentration of the known crystal form or the amorphous form of Dabrafenib in the mixed solvent of water and organic solvent is 0.1~5 mg/mL, and more preferably, 0.1~3 mg/mL;

Preferably, the duration of crystallizing is 1~3 weeks.

(3) Adding water or a water-saturated $C_5$~$C_8$ alkane solution into a solution of a known crystal form or an amorphous form of Dabrafenib in an organic solvent, stirring to crystallize for 3~14 days, separating and drying the precipitated crystal to get Crystal Form VI of Dabrafenib, wherein the organic solvent is selected from $C_1$~$C_4$ alcohols, $C_4$~$C_5$ esters, $C_2$~$C_5$ ethers, $C_3$~$C_4$ ketones, tetrahydrofuran, nitromethane, acetonitrile, or their mixtures;

Preferably, the known crystal form of Dabrafenib is the Known Crystal Form 2 of Dabrafenib;

Preferably, the organic solvent is selected from methanol, ethanol, propanol, butanol, ethyl acetate, isopropyl acetate, ethyl ether, methyl tert-butyl ether, acetone, butanone, tetrahydrofuran, nitromethane or acetonitrile;

Preferably, $C_5$~$C_8$ alkane is selected from cyclohexane, methyl cyclohexane, n-hexane, n-heptane or their mixtures; and more preferably, $C_5$~$C_8$ alkane is selected from methyl cyclohexane or n-heptane;

Preferably, the volume ratio of water or water-saturated $C_5\sim C_8$ alkane solution to the organic solvent is 0.1:1~100:1, and more preferably, 0.5:1~50:1;

Preferably, the amount of the known crystal form or the amorphous form of Dabrafenib in the solution is 0.1-1 times of its solubility in the organic solvent at the operation temperature, and more preferably, 0.5~1 times;

Preferably, the operation temperature is room temperature to 60° C., and more preferably, room temperature;

Preferably, the duration of crystallizing is 3~7 days.

(4) Preparing a solution of the known crystal form or an amorphous form of Dabrafenib in a mixed solvent of water and an organic solvent at high temperature, cooling and stirring the solution to crystallize, separating and drying the precipitated crystals to get Crystal Form VI of Dabrafenib, wherein the organic solvent is selected from $C_1\sim C_4$ alcohols, $C_4\sim C_5$ esters, $C_2\sim C_5$ ethers, $C_3\sim C_4$ ketones, tetrahydrofuran, nitromethane, acetonitrile or their mixtures;

Preferably, the known crystal form of Dabrafenib is the Known Crystal Form 2 of Dabrafenib;

Preferably, the organic solvent is selected from methanol, ethanol, propanol, butanol, ethyl acetate, isopropyl acetate, ethyl ether, methyl tert-butyl ether, acetone, butanone, tetrahydrofuran, nitromethane or acetonitrile;

Preferably, the volume content of water in the mixed solvent of water and an organic solvent is at least 0.01%~50%, and more preferably, 0.1%~50%; generally, if water is slightly soluble or poorly soluble in the selected organic solvent, then the volume content of water in the mixed solvents will be 0.01%~ of the maximum solubility of water in such solvent; and more preferably, 0.1%~ of the maximum solubility of water in such solvent;

Preferably, the amount of the known crystal form or the amorphous form of Dabrafenib in the solution is 0.1-1 times of its solubility in the organic solvent at high temperature, and more preferably, 0.5~1 times;

Preferably, the high temperature is 40° C. to the boiling point of the mixed solvents, and more preferably 50~80° C.; and the temperature after cooling is 0° C. to room temperature, and preferably, room temperature;

Preferably, the duration of crystallizing is 3~14 days, and more preferably, 3~7 days.

In the above preparation methods (1)~(4) of Crystal Form VI of Dabrafenib, the drying temperature is room temperature to 60° C., and preferably, 40° C.; the drying time is 1~48 h, and preferably 1~24 h.

In the above preparation methods (1)~(4) of Crystal Form VI of Dabrafenib:

The mentioned organic solvents are miscible with water and the proportion of miscible solvents is based on the mutual solubility of solvents;

C1~C4 alcohols include methanol, ethanol, n-propanol, isopropanol, n-butanol and sec-butanol;

C4~C5 esters include ethyl acetate and isopropyl acetate;

C2~C5 ethers include ethyl ether and methyl tert-butyl ether;

C3~C4 ketones include acetone and butanone;

C5~C8 alkane include cyclohexane, methyl cyclohexane, n-hexane and n-heptane.

The preparation method of water-saturated organic solvent solution comprises: taking equal volume of the organic solvent and water, stirring for 2~5 h at room temperature and then collecting the organic layer.

Crystal Form VI has the following beneficial properties:

(1) When Crystal Form VI was stored for 3 months in a desiccator at room temperature, or in a drying oven at 40° C., or at room temperature and 97% RH, or at room temperature and 75% RH or at room temperature and 44% RH, its crystal form did not change.

(2) The mass change of Crystal Form VI is only about 0.5% between 20~80% RH and its hygroscopicity is lower than that of the Known Crystal Form 1 (whose mass change is 1.9% between 20~80% RH).

(3) Crystal Form VI is the most stable crystal form in the existence of water. According to the research of the inventors, it is found that the Known Crystal Form 1, the Known Crystal Form 2 and all the other crystal forms disclosed in the present invention are unstable when stirred in water or aqueous ethanol solution at room temperature or high temperature (40° C.), and form conversion happens, Crystal Form VI keeps its form unchanged under the same conditions.

(4) Crystal Form VI is the most stable crystal form in the wet granulation process or in the suspension. In the wet granulation process or in the suspension, the Known Crystal Form 1, the Known Crystal Form 2 and all the other crystal forms disclosed in the present invention are unstable and their crystal forms converts; however, Crystal Form VI keeps its form unchanged in the wet granulation process or in the suspension.

The above properties of Crystal Form VI show that compared with the Known Crystal Form 1 and the Known Crystal Form 2 of Dabrafenib, Crystal Form VI of Dabrafenib of the present invention has good form stability and low hygroscopicity, therefore it can better deal with problems such as poor content uniformity, decreased purity, which were caused by time, humidity and other factors during manufacture, storage and transportation, and it can effectively mitigate the risk of reduced treatment effect and safety risk arising from the form changes of active substances, content variations and/or increasing in impurity content; moreover, Crystal Form VI of the present invention is the most stable crystal form in aqueous systems, and is well suitable for the wet granulation process or to be made into the suspensions; and it has excellent processability, good production reproducibility and is beneficial to the storage and transportation in the late period. (As the Known Crystal Form 3 is extremely unstable, it is not used for comparison in the present invention.)

According to the purpose of the present invention, Crystal Form VII of Dabrafenib (hereinafter referred to as "Crystal Form VII") is also provided.

Measured using Cu—Kα radiation, Crystal Form VII is characterized by a X-ray powder diffraction pattern having the specific peaks at the diffraction angle 2θ of 7.9±0.2°, 14.5±0.2°, 19.4±0.2° and 24.3±0.2°.

In one preferred embodiment of the present invention, Crystal Form VII is characterized by a X-ray powder diffraction pattern having the specific peaks at the diffraction angle 2θ of 7.9±0.2°, 11.6±0.2°, 14.5±0.2°, 17.7±0.2°, 19.4±0.2°, 20.6±0.2°, 24.3±0.2°, 27.8±0.2°, 29.2±0.2°, 30.1±0.2° and 32.6±0.2°.

In the further preferred embodiment of the present invention, Crystal Form VII is characterized by a X-ray powder diffraction pattern having the specific peaks at the diffraction angle 2θ of 7.9±0.2°, 11.6±0.2°, 13.7±0.2°, 14.5±0.2°, 16.3±0.2°, 17.7±0.2°, 19.4±0.2°, 20.6±0.2°, 24.3±0.2°, 25.3±0.2°, 25.5±0.2°, 27.8±0.2°, 29.2±0.2°, 30.1±0.2° and 32.6±0.2°.

In the even further preferred embodiment of the present invention, Crystal Form VII is characterized by a X-ray powder diffraction pattern having the following specific peaks at the diffraction angle 2θ and their relative intensities:

| Diffraction angle 2θ | Relative intensity % |
|---|---|
| 7.9 ± 0.2° | 34.2 |
| 11.6 ± 0.2° | 16.2 |
| 13.7 ± 0.2° | 6.7 |
| 14.5 ± 0.2° | 38.1 |
| 16.3 ± 0.2° | 6.7 |
| 17.7 ± 0.2° | 15.1 |
| 19.4 ± 0.2° | 27.6 |
| 20.6 ± 0.2° | 12.9 |
| 24.3 ± 0.2° | 100.0 |
| 25.3 ± 0.2° | 6.6 |
| 25.5 ± 0.2° | 5.9 |
| 27.8 ± 0.2° | 14.8 |
| 29.2 ± 0.2° | 11.4 |
| 30.1 ± 0.2° | 9.2 |
| 32.6 ± 0.2° | 7.5 |

Non-restrictively, in one specific embodiment of the present invention, Crystal Form VII of Dabrafenib is characterized by a X-ray powder diffraction pattern as shown in FIG. 8.

Crystal Form VII may be prepared by any one of the following methods:

(1) At room temperature, adding water or a $C_5$~$C_8$ alkane into an organic solvent solution made from a known crystal form or an amorphous form of Dabrafenib, stirring to crystallize for 1~60 mins, separating and drying the precipitated crystal to get Crystal Form VII of Dabrafenib, wherein the organic solvent is selected from ethyl ether, 1,4-dioxane or $C_2$~$C_3$ alcohols;

Preferably, the known crystal form of Dabrafenib is the Known Crystal Form 2 of Dabrafenib;

Preferably, the organic solvent is selected from ethanol, isopropanol, ethyl ether or 1,4-dioxane;

Preferably, $C_5$~$C_8$ alkane is selected from cyclohexane, methyl cyclohexane, n-hexane, n-heptane or their mixtures; and more preferably, $C_5$~$C_8$ alkane is selected from methyl cyclohexane or n-heptane;

Preferably, the volume ratio of water or $C_5$~$C_8$ alkane to the organic solvent is 0.1:1~100:1, more preferably, 0.5:1~50:1, and the most preferably, 0.5:1~5:1;

Preferably, the amount of the known crystal form or the amorphous form of Dabrafenib in the solution is 0.1-1 times of its solubility in the organic solvent at room temperature, and more preferably, 0.5~1 times;

Preferably, the duration of crystallizing is 1~30 mins.

(2) At room temperature, placing the isopropyl acetate solution of a known crystal form or an amorphous form of Dabrafenib in a sealed atmosphere full of the diffusive solvent to crystallize, separating and drying the precipitated crystals to get Crystal Form VII of Dabrafenib, wherein the diffusive solvent is the volatile ether solvent;

Preferably, the known crystal form of Dabrafenib is the Known Crystal Form 2 of Dabrafenib;

Preferably, the diffusive solvent is mineral ether or isopropyl ether;

Preferably, the concentration of the isopropyl acetate solution is 0.1~5 mg/mL, and more preferably, 0.1~3 mg/mL;

Preferably, the duration of crystallization is 1~3 weeks.

(3) At room temperature, putting an amorphous form of Dabrafenib into a $C_3$~$C_4$ alcohol to form a suspension, stirring to crystallize, separating and drying the precipitated crystals to get Crystal Form VII of Dabrafenib;

Preferably, the amount of the amorphous form of Dabrafenib is 1.1~20 times of its solubility in a $C_3$~$C_4$ alcohol at room temperature, and more preferably, 1.5~10 times;

Preferably, $C_3$~$C_4$ alcohol is selected from isopropanol, n-propanol, n-butanol or sec-butanol;

Preferably, the duration of crystallization is 0.1~10 hours, and more preferably, 0.1~2 hours.

(4) Raising the temperature of Crystal Form VI of Dabrafenib until its crystal water is completely removed, then cooling naturally to room temperature to get Crystal Form VII of Dabrafenib; preferably, the temperature is raised to 125° C. at the speed of 10° C./min.

(5) Evaporating the ethyl acetate solution of a known crystal form or an amorphous form of Dabrafenib to crystallize, separating and drying the precipitated crystals to get Crystal Form VII of Dabrafenib;

Preferably, the known crystal form of Dabrafenib is the Known Crystal Form 2 of Dabrafenib;

Preferably, the amount of the known crystal form or the amorphous form of Dabrafenib in the ethyl acetate solution is 0.1~1 times of its solubility in ethyl acetate at room temperature, and more preferably, 1.5~1 times.

Preferably, the duration of crystallizing is 1~7 days, and more preferably 3~7 days.

Crystal Form VII has the following beneficial properties:

(1) The mass change of Crystal Form VII is only about 0.1% between 20~80% RH and its hygroscopicity is lower than that of the Known Crystal Form 1 (whose mass change is 1.9% between 20~80% RH);

(2) When Crystal Form VII is stored for 3 months in a desiccator at room temperature, at room temperature and 97% RH, at room temperature and 75% RH, at room temperature and 44% RH or in a drying oven at 40° C., its crystal form does not change;

(3) Competitive slurring of Crystal Form VII and the Known Crystal Form 1 in purified water indicates that Crystal Form VII is more stable than the Known Crystal Form 1;

(4) Crystal Form VII is of rod-shaped particles, which have larger particle size than those of the Known Crystal Form 1 and the Known Crystal Form 2; and the flowability of such particles is good.

The above properties of Crystal Form VII show that, compared with the Known Crystal Form 1 and the Known Crystal Form 2 of Dabrafenib, Crystal Form VII of Dabrafenib in the present invention has good form stability and low hygroscopicity, so it can better deal with the problems such as poor content uniformity, decreased purity, caused by time, humidity and other factors during manufacture, storage and transportation, it can effectively mitigate the risk of reduced treatment effect and the safety risk arising from the form changes of the active substance, content variations and/or increasing in impurity. Moreover, compared with the Known Crystal Form 1 and the Known Crystal Form 2 of Dabrafenib, Crystal Form VII of the present invention has good particle morphology and good flow properties which are beneficial for accurate quantification and process, and it has good production reproducibility and excellent suitability for the formulation process. (As the Known Crystal Form 3 is extremely unstable, it is not used for comparison in the present invention.)

By providing the new Crystal Form VI or Crystal Form VII of Dabrafenib in the present invention, the problems of crystal forms in the prior art have been solved. Compared with the known crystal forms, the new crystal form has at least one or more beneficial properties, such as higher crystallinity, solubility, dissolution rate, good morphology, less tendency to convert to other forms and/or to dehydrate, good thermal stability and mechanical properties, low hygroscopicity, better flowability and compressibility, improved bulk density and storage stability, low content of residual solvent, etc.

In addition, according to the purpose of the present invention, Crystal Form III of Dabrafenib (hereinafter referred to as "Crystal Form III") is also provided.

Measured using Cu—Kα radiation, Crystal Form III is characterized by a X-ray powder diffraction pattern having the specific peaks at the diffraction angle 2θ of 10.3±0.2°, 12.9±0.2°, 17.5±0.2°, 21.7±0.2° and 25.1±0.2θ.

Further, Crystal Form III is characterized by a X-ray powder diffraction pattern also having the specific peaks at the diffraction angle 2θ of 7.8±0.2°, 11.0±0.2°, 15.9±0.2°, 16.9±0.2°, 18.1±0.2°, 18.6±0.2°, 20.9±0.2°, 21.3±0.2°, 25.7±0.2°, 26.0±0.2°, 27.2~0.2°, 27.6±0.2°, 30.9±0.2°, 31.8±0.2° and 33.9±0.2°.

Non-restrictively, measured using Cu—Kα radiation, Crystal Form III is characterized by a X-ray powder diffraction pattern substantially as shown in FIG. 15.

Crystal Form III may be prepared by the following method: Suspending a known crystal form or an amorphous form of Dabrafenib in sec-butanol to form a suspension, stirring to crystallize, and then separating the precipitated crystals without drying to get Crystal Form III of Dabrafenib;

Preferably, the known crystal form of Dabrafenib is the Known Crystal Form 2 of Dabrafenib;

Preferably, the amount of the known crystal form or the amorphous form of Dabrafenib is 2~100 times of its solubility in sec-butanol at the operation temperature, and more preferably, 2~10 times;

Preferably, the operation temperature is room temperature to 60° C., and more preferably, room temperature;

Preferably, the duration of crystallization is 3~14 days, and more preferably 3~7 days.

In addition, according to the purpose of the present invention, Crystal Form IV of Dabrafenib (hereinafter referred to as "Crystal Form IV") is also provided.

Measured using Cu—Kα radiation, Crystal Form IV is characterized by a X-ray powder diffraction pattern having the specific peaks at the diffraction angle 2θ of 5.9±0.2°, 6.6±0.2°, 12.0±0.2°, 18.1±0.2° and 24.3±0.2°.

Further, Crystal Form IV is characterized by a X-ray powder diffraction pattern also having the specific peaks at the diffraction angle 2θ of 7.9±0.2°, 8.9±0.2°, 11.7±0.2°, 14.5±0.2°, 16.2±0.2°, 16.5±0.2°, 17.8±0.2°, 19.4±0.2°, 20.3±0.2°, 20.6±0.2°, 21.2±0.2°, 22.3±0.2°, 25.4±0.2°, 25.6±0.2°, 26.9±0.2°, 27.8±0.2°, 28.2±0.2°, 28.4±0.2° and 29.2±0.2°.

Non-restrictively, measured using Cu—Kα radiation, Crystal Form IV is characterized by a X-ray powder diffraction pattern substantially as shown in FIG. 16.

Crystal Form IV may be prepared by the following method: Volatilizing the methyl tert-butyl ether solution of a known crystal form or an amorphous form of Dabrafenib to crystallize, separating the precipitated crystal without drying to get Crystal Form IV of Dabrafenib;

Preferably, the known crystal form of Dabrafenib is the Known Crystal Form 2 of Dabrafenib;

Preferably, the amount of the known crystal form or the amorphous form of Dabrafenib in the methyl tert-butyl ether solution is 0.1~1 times of its solubility in methyl tert-butyl ether at room temperature, and more preferably, 0.5~1 times;

Preferably, the duration of crystallization is 1~7 days, and more preferably 3~7 days.

In addition, according to the purpose of the present invention, Crystal Form V of Dabrafenib (hereinafter referred to as "Crystal Form V") is also provided.

Measured using Cu—Kα radiation, Crystal Form V is characterized by a X-ray powder diffraction pattern having the specific peaks at the diffraction angle 2θ of 9.3±0.2°, 13.4±0.2°, 16.5±0.2°, 19.8±0.2° and 21.3±0.2°.

Furthermore, Crystal Form V is characterized by a X-ray powder diffraction pattern also having the specific peaks at the diffraction angle 2θ of 8.2±0.2°, 11.8±0.2°, 12.6±0.2°, 14.5±0.2°, 16.0±0.2°, 20.7±0.2°, 20.9±0.2°, 21.7±0.2°, 22.4±0.2°, 22.7±0.2°, 23.5±0.2°, 24.5±0.2°, 24.9±0.2°, 25.2±0.2°, 25.5±0.2°, 25.8±0.2°, 26.6±0.2°, 26.9±0.2°, 27.2±0.2°, 29.2±0.2°, 30.4±0.2° and 32.9±0.2°.

Non-restrictively, measured using Cu—Kα radiation, Crystal Form V is characterized by a X-ray powder diffraction pattern substantially as shown in FIG. 17.

Crystal Form V may be prepared by the following method: Suspending a known crystal form or an amorphous form of Dabrafenib in dichloromethane to form a suspension, stirring to crystallize, and then separating the precipitated crystals without drying to get Crystal Form V of Dabrafenib;

Preferably, the known crystal form of Dabrafenib is the Known Crystal Form 2 of Dabrafenib;

Preferably, the amount of the known crystal form or the amorphous form of Dabrafenib is 2~100 times of its solubility in dichloromethane at the operation temperature, and more preferably, 2~10 time;

Preferably, the operation temperature is room temperature to 60° C., and more preferably, room temperature;

Preferably, the duration of crystallization is 3~14 days, and more preferably 3~7 days.

In addition, according to the purpose of the present invention, Crystal Form VIII of Dabrafenib (hereinafter referred to as "Crystal Form VIII") is also provided.

Measured using Cu—Kα radiation, Crystal Form VIII is characterized by a X-ray powder diffraction pattern having the specific peaks at the diffraction angle 2θ of 9.6±0.2°, 14.2±0.2°, 19.5±0.2°, 20.4±0.2° and 20.9±0.2°.

Furthermore, Crystal Form VIII is characterized by a X-ray powder diffraction pattern also having the specific peaks at the diffraction angle 2θ of 3.5±0.2°, 12.2±0.2°, 13.7±0.2°, 13.9±0.2°, 14.7±0.2°, 15.0~0.2°, 15.5±0.2°, 16.2±0.2°, 16.5±0.2°, 17.0±0.2°, 19.0±0.2°, 21.7±0.2°, 22.0±0.2°, 22.3±0.2°, 23.6±0.2°, 24.2±0.2°, 24.4±0.2°, 24.6±0.2°, 29.0±0.2° and 30.2±0.2°.

Non-restrictively, measured using Cu—Kα radiation, Crystal Form VIII is characterized by a X-ray powder diffraction pattern substantially as shown in FIG. 18.

In addition, according to the purpose of the present invention, Crystal Form VIIIa of Dabrafenib (hereinafter referred to as "Crystal Form VIIIa") is also provided.

Measured using Cu—Kα radiation, Crystal Form VIIIa is characterized by a X-ray powder diffraction pattern having the specific peaks at the diffraction angle 2θ of 3.5±0.2°, 9.8±0.2°, 12.2±0.2° and 16.4±0.2°.

Furthermore, Crystal Form VIIIa is characterized by a X-ray powder diffraction pattern also having the specific peaks at the diffraction angle 2θ of 7.2±0.2°, 8.3±0.2°, 9.2±0.2°, 11.2±0.2°, 13.2±0.2°, 13.9±0.2°, 14.7±0.2°, 18.4~0.2°, 19.1±0.2°, 19.8±0.2°, 21.5±0.2°, 22.1±0.2°, 24.2±0.20°, 24.7±0.2°, 26.0±0.2° and 29.7±0.2°.

Non-restrictively, measured using Cu—Kα radiation, Crystal Form VIIIa is characterized by a X-ray powder diffraction pattern substantially as shown in FIG. 21.

Crystal Form VIII and Crystal Form VIIIa may be prepared by the following method: At room temperature, placing the ethyl acetate solution of a known crystal form or an amorphous form of Dabrafenib in a sealed atmosphere full of isopropyl ether to crystallize, separating the precipitated crystals without drying to get Crystal Form VIIIa of Dabrafenib; keeping the separated crystals still for 2 h at room temperature to get Crystal Form VIII;

Preferably, the known crystal form of Dabrafenib is the Known Crystal Form 2 of Dabrafenib;

Preferably, the concentration of the ethyl acetate solution is 0.1~5 mg/mL, and more preferably, 0.1~3 mg/mL;

Preferably, the duration of crystallization is 1~7 weeks.

In addition, according to the purpose of the present invention, Crystal Form Ie of Dabrafenib (hereinafter referred to as "Crystal Form Ie") is also provided.

Measured using Cu—Kα radiation, Crystal Form Ie is characterized by a X-ray powder diffraction pattern having the specific peaks at the diffraction angle 2θ of 7.9±0.20°, 10.5±0.2°, 15.2±0.2°, 20.5±0.2° and 20.8±0.2°.

Furthermore, Crystal Form Ie is characterized by a X-ray powder diffraction pattern also having the specific peaks at the diffraction angle 2θ of 3.9±0.2°, 9.5±0.2°, 10.0±0.2°, 11.4±0.2°, 12.5±0.2°, 13.3±0.2°, 14.3±0.2°, 16.1±0.2°, 16.6±0.2°, 17.4±0.2°, 17.9±0.2°, 18.3±0.2°, 19.7±0.2°, 20.2±0.2°, 22.2±0.2°, 22.7±0.2°, 23.8±0.2°, 24.4±0.2°, 25.2±0.2°, 25.9±0.2°, 26.2±0.2°, 28.3±0.2° and 29.5±0.2°.

Non-restrictively, measured using Cu—Kα radiation, Crystal Form Ie is characterized by a X-ray powder diffraction pattern substantially as shown in FIG. 19.

Crystal Form Ie may be prepared by any one of the following methods:

1) Suspending an amorphous form of Dabrafenib in toluene to form a suspension, stirring to crystallize, and then separating the precipitated crystals without drying to get Crystal Form Ie;

Preferably, the amount of the amorphous form of Dabrafenib is 2~100 times of its solubility in toluene at the operation temperature, and more preferably, 2~10 times;

Preferably, the operation temperature is room temperature to 60° C., and more preferably, room temperature;

Preferably, the duration of crystallization is 0.1~2 hours.

2) Preparing the toluene solution containing a known crystal form or an amorphous form of Dabrafenib at high temperature, cooling the solution rapidly and stirring to crystallize, and then separating the precipitated crystal without drying to get Crystal Form Ie;

Preferably, the known crystal form of Dabrafenib is the Known Crystal Form 2 of Dabrafenib;

Preferably, the amount of the known crystal form or the amorphous form of Dabrafenib is 0.1~1 times of its solubility in toluene at high temperature, and more preferably, 0.5~1 times;

Preferably, the duration of crystallization is 0.1~2 hours;

Preferably, the high temperature is 40° C. to the boiling point of toluene, and more preferably 50~80° C.; and the temperature after cooling is 0° C. to room temperature, and preferably, room temperature.

In addition, according to the purpose of the present invention, Crystal Form VIIb of Dabrafenib (hereinafter referred to as "Crystal Form VIIb") is also provided.

Measured using Cu—Kα radiation, Crystal Form VIIb is characterized by a X-ray powder diffraction pattern having the specific peaks at the diffraction angle 2θ of 9.8±0.2°, 11.4±0.2°, 12.2±0.2°, 15.9±0.2° and 21.4±0.2°.

Furthermore, Crystal Form VIIb is characterized by a X-ray powder diffraction pattern also having the specific peaks at the diffraction angle 2θ of 6.7±0.2°, 7.8±0.2°, 10.3±0.2°, 12.9±0.2°, 14.5±0.2°, 14.8±0.2°, 17.2±0.2°, 17.5±0.2°, 18.8±0.2°, 19.2±0.2°, 20.3±0.2°, 21.0±0.2°, 22.1±0.2°, 24.2±0.2° and 30.4±0.2°.

Non-restrictively, measured using Cu—Kα radiation, Crystal Form VIIb is characterized by a X-ray powder diffraction pattern substantially as shown in FIG. 20.

Crystal Form VIIb may be prepared by the following method: Adding methyl cyclohexane into the butanone solution of a known crystal form or an amorphous form of Dabrafenib, stirring to crystallize, and then separating the precipitated crystals without drying to get Crystal Form VIIb;

Preferably, the known crystal form of Dabrafenib is the Known Crystal Form 2 of Dabrafenib;

Preferably, the amount of the known crystal form or the amorphous form of Dabrafenib in the solution is 0.1-1 times of its solubility in butanone at the operation temperature, and more preferably, 0.5~1 times;

Preferably, the volume ratio of methyl cyclohexane to butanone is 0.1:1~10:1, and more preferably, 0.5:1~5:1;

Preferably, the operation temperature is room temperature to 60° C., and more preferably, room temperature;

Preferably, the duration of crystallizing is 3~14 days, and more preferably 3~7 days.

By providing the new Crystal Form III, Crystal Form IV, Crystal Form V, Crystal Form VIII, Crystal Form Ie, Crystal Form VIIb or Crystal Form VIIIa of Dabrafenib in the present invention, the problems of crystal forms in the prior art have been solved. Each new crystal form has at least one of the following beneficial properties: better thermal stability, good morphology, low hygroscopicity, better flowability, better apparent density and better storage stability.

In the preparation methods of Crystal Form VI, Crystal Form VII, Crystal Form III, Crystal Form IV, Crystal Form V, Crystal Form VIII, Crystal Form Ie, Crystal Form VIIb and Crystal Form VIIIa in the present invention:

The mentioned "the Known Crystal Form of Dabrafenib" includes but not limited to the Known Crystal Form 1, the Known Crystal Form 2, the Known Crystal Form 3 of Dabrafenib or their mixtures.

The mentioned "Room Temperature" refers to 15~25° C.

The mentioned "Stirring" is accomplished with the routine methods in this field, such as magnetic stirring or mechanical stirring; the stirring speed is 50~1,800 rpm, and preferably, 300~900 rpm.

The mentioned "Separating" is accomplished with the routine methods in this field, such as centrifugation or filtration. The operation of "centrifugation" is as follows: place the sample to be separated in the centrifugal tube and centrifugate it at 6,000 rpm until all the solids settle down on the bottom of the centrifugal tube. "Filtration" generally refers to the suction filtration at the pressure less than the atmospheric pressure; and the preferable pressure is less than 0.09 MPa.

Unless otherwise specified, the mentioned "Drying" may be conducted at room temperature or higher temperature. The drying temperature is room temperature to about 60° C., or to 40° C., or to 50° C. The drying time may be 2~48 hours, or overnight. "Drying" may be conducted in a fume hood, a blast drying oven or a vacuum drying oven.

The mentioned "Sealed Atmosphere" is operated as follows: place a small uncovered 20 mL-vial filled with the prepared solution into a 100 mL sealed glass bottle which was prefilled with 10~30 mL diffusive solvent, after the diffusive solvent diffused for 1~3 weeks into the vial, separate the precipitated solids.

In the present invention, "Crystal" or "Crystal Form" refers to the crystal or the crystal form being identified by the X-ray diffraction pattern shown herein. The scientists in this field are able to understand that physical and chemical properties discussed herein can be characterized, wherein the experimental errors depend on the conditions of instruments, the sample preparations and the purity of samples. In particular, the scientists in this field generally know that the X-ray diffraction pattern usually may change with the change of the experimental conditions. It is necessary to point out that, the relative intensity of the X-ray diffraction pattern is likely to change with the change of the experimental conditions; therefore, the sequence of peak intensity cannot be regarded as the only or the determining factor. Moreover, generally, the experimental errors of the peak angles are 5% or less, so such errors shall be considered and generally the allowed errors are ±0.2° 2θ. In addition, due to the effect of the experimental factors including sample height, peak angles may have an overall shifting; generally, certain shifting is allowed. Hence, the scientists in this field may understand that, it is unnecessary that the X-ray diffraction pattern of a crystal form in the present invention should be exactly the same with X-ray diffraction patterns of the example shown herein. Any crystal forms whose X-ray diffraction pattern have the same or similar characteristic peaks should be within the scope of the present invention. The scientists in this field can compare the patterns shown in the present invention with that of an unknown crystal form in order to identify whether these two groups of patterns reflect the same or different crystal forms.

"Crystal Form" and "Polymorphic Form" as well as other related terms in the present invention refer to the solid compounds whose crystal structure is being in a special crystal form state. The difference in the physical and chemical properties of the polymorphic forms may be embodied in storage stability, compressibility, density, dissolution rate, etc. In extreme cases, the difference in solubility or dissolution rate may result in inefficient drugs, even developing toxicitys.

Unless otherwise specified, the "Anhydrate" mentioned in the present invention refers to the crystal form with its water content no more than 1.5% (weight ratio) or 1.0% (weight ratio) measured by TGA.

In some embodiments, the new crystal forms in the present invention, including Crystal Forms VI, VII, III, IV, V, VIII, Ie, VIIb and VIIIa, are pure, substantially not contaminated with any other crystal forms. In particular, Crystal Forms VI and VII are substantially not contaminated with any other crystal forms. In the present invention, when used to refer to the new crystal form, "substantially not" means that the crystal form contains less than 20% (weight) of the other crystal forms; further, less than 10% (weight); furthermore, less than 5% (weight); and the furthest, less than 1% (weight).

Generally, Crystal Forms VI, VII, III, IV, V, VIII, Ie, VIIb and VIIIa substantially do not contain either the Known Crystal Form 1, or the Known Crystal Form 2 or the Known Crystal Form 3; in particular, these crystal forms have no characteristic peaks of the Known Crystal Form 1 at 9.5±0.2°, 10.1±0.2°, 12.7±0.2°, 16.1±0.20 and 19.0±0.20, and have no characteristic peaks of the Known Crystal Form 2 at 7.9±0.2°, 13.6±0.2°, 14.6±0.2°, 15.8±0.2°, 20.3±0.2° and 21.9±0.2°, and have no characteristic peaks of the Known Crystal Form 3 at 12.2±0.2°, 12.8~0.2°, 15.9±0.2°, 21.3±0.20 and 24.9±0.2°.

The polymorphic forms of drugs may be obtained by the methods including but not limited to the following: melting and recrystallization, melting and cooling, solvent recrystallization, desolvation, rapid volatilization, rapid cooling, slow cooling, vapor diffusion and sublimation. The polymorphic form may be tested, discovered and classified via X-ray powder diffraction (XRPD), differential scanning calorimetry (DSC), thermogravimetric analysis (TGA), optical microscopy, hygroscopicity, etc.

The crystallization methods for the crystal forms of the present invention include evaporation at room temperature, slurry, cooling and recrystallization, diffusion and anti-solvent recrystallization.

Evaporation at room temperature means, for example, putting the clear solution of the sample into an uncovered 5 mL-vial and evaporate at room temperature, with or without nitrogen purge.

Slurry means, for example, stirring the over-saturated solution (with the presence of insoluble solids) of the sample in a solvent system to crystallize, generally for 2 hours~2 weeks.

Cooling and recrystallization means, for example, under certain high temperature conditions, dissolving the sample in suitable solvent(s), putting the solution into a 5 mL-vial, placing the vial in a temperature-variable shaker, then cooling it in turn at certain cooling rate and stirring overnight. The experimental temperature may be 75~0° C. and preferably 50~15° C. At each specific temperature, the sample solution is kept warm for 2 hours~2 days.

Diffusion means, for example, dissolving the sample in a good solvent and then placing the solution in a sealed atmosphere full of the volatile solvent to recrystallize.

Anti-solvent recrystallization means, for example, dissolving the sample in a good solvent, adding an appropriate amount of anti-solvent, and then stirring to recrystallize.

In addition, the present invention provides a pharmaceutical composition, which comprises a therapeutically and/or preventively effective amount of one or more selected from, including Crystal Form VI, Crystal Form VII, Crystal Form III, Crystal Form IV, Crystal Form V, Crystal Form VIII, Crystal Form Ie, Crystal Form VIIb or Crystal Form VIIIa of Dabrafenib of the present invention, and at least one pharmaceutically acceptable excipient. Moreover, the pharmaceutical composition may also comprise pharmaceutical acceptable other crystal forms or the amorphous form of Dabrafenib or its salts, and such crystal forms include but not limited to the Known Crystal Form 1, the Known Crystal Form 2 and the Known Crystal Form 3. Optionally, the pharmaceutical composition may also comprise one or more of other pharmaceutical active ingredients, such as any treatment drugs having the activity to treat sensitive tumors.

The above pharmaceutical composition may be prepared in certain forms and be administered by suitable routes, such as oral, parenteral (including subcutaneous, intramuscular, intravenous or intradermal), rectal, transdermal, nasal, vaginal, etc. The suitable pharmaceutical dosage forms for oral route include tablets, capsules, granules, pulvisie, pills, powders, pastilles, solutions, syrups, suspensions, etc, which, according to the actual demand, may be suitable for rapid release, delayed release or adjustable release of pharmaceutical active ingredients. The suitable pharmaceutical dosage forms for parenteral routes include aqueous or non-aqueous sterile injectable solutions, emulsions or suspensions. The suitable pharmaceutical dosage forms for rectal routes include suppository or enema. The suitable pharmaceutical dosage forms for transdermal routes include ointments, creams and patches. The suitable pharmaceutical dosage forms for nasal routes include aerosols, sprays and nasal drops. The suitable pharmaceutical dosage forms for vaginal routes include suppository, plug agents, gels, pastes or sprays. Preferably, as the crystal forms of the present invention have unexpected low hygroscopicity and good stability in water or aqueous ethanol solution, they are particularly suitable for the preparation of tablets, suspensions, capsules, disintegrating tablets, immediate release tablets, slow release tablets and controlled release tablets; and more preferably, tablets, suspensions and capsules.

The pharmaceutically acceptable excipients in the above pharmaceutical composition, in case of the oral solid form, include but not limited to: diluents, such as starch, pregelatinized starch, lactose, powdered cellulose, microcrystalline cellulose, bicalcium phosphate, tricalcium phosphate, mannitol, sorbitol, and sugar; binders, such as Arabia gum, guar gum, gelatin, polyvinylpyrrolidone, hydroxypropyl cellulose, hydroxypropyl methylcellulose, and polyethylene glycol; disintegrating agents, such as starch, sodium starch glycolate, pregelatinized starch, cross-linked polyvinylpyrrolidone, cross-linked sodium carboxymethylcellulose, and colloidal silicon dioxide; lubricants, such as stearic acid, magnesium stearate, zinc stearate, sodium benzoate, and sodium acetate; flow aids, such as colloidal silicon dioxide; complex-forming agents, such as cyclodextrins and resins of various levels; release rate controlling agents, such as hydroxypropyl cellulose, carboxymethyl cellulose, hydroxypropyl methyl cellulose, ethyl cellulose, methyl cellulose, methyl methacrylate, and wax. The other useable pharmaceutical acceptable excipients include but not limited to film-forming agent, plasticizer, coloring agent, flavoring agent, viscosity regulator, preservative and antioxidant, etc. Optionally, tablets are coated with the coating layer; for example, providing shellac isolating coating, sugar coating or polymer coating. The coating layer may contain polymers such as hydroxypropyl methyl cellulose, polyvinyl alcohol, ethyl cellulose, methyl acrylic polymer, hydroxypropyl cellulose or starch, and may also contain antiadherents, such as silica, talcum powder; opacifying agents, such as titanium dioxide; colorants, such as iron oxide. In case of the oral liquid form, the suitable excipients include water, oils, alcohol, glycol, flavoring agents, preservatives, stabilizers and colorants. The aqueous or non-aqueous sterile suspensions may contain suspending agents and thickeners. The suitable excipients for the aqueous suspension include synthetic gum or natural gum, such as Arabia gum, Cocklebur gum, alginate, glucan, sodium carboxymethyl cellulose, methyl cellulose, polyvinyl pyrrolidone or gelatin. In case of parenteral route dosage forms, the excipients in aqueous or non-aqueous sterile injection solutions generally are sterile water, normal saline or dextrose in water, and may contain buffering agent, antioxidant, antibacterial agent, and the solutes which enable the pharmaceutical composition isotonic with blood, etc. Each excipient must be acceptable, be compatible with the other ingredients in the formula and harmless to patients.

The pharmaceutical composition may be prepared by the methods in the art known to the scientists in this field. When preparing the pharmaceutical composition, mix Crystal Form VI, Crystal Form VII, Crystal Form III, Crystal Form IV, Crystal Form V, Crystal Form VIII, Crystal Form Ie, Crystal Form VIIb or Crystal Form VIIIa of Dabrafenib of the present invention with one or more pharmaceutically acceptable excipients, and optionally, mix with one or more of other active pharmaceutical ingredients. For example, tablets, capsules and granules may be prepared with such technologies as mixing, granulation, tableting, capsule filling, etc; powders may be prepared by mixing the pulverized active pharmaceutical ingredients with suitable size and excipients; solutions and syrups may be prepared by dissolving active pharmaceutical ingredients into the appropriately flavored water or aqueous solution; suspensions may be prepared by dispersing active pharmaceutical ingredients in the pharmaceutically acceptable carriers.

What should be specially mentioned is the wet granulation process for solid preparations. With the wet granulation of tablets as the example, the preparation process is as follows: mix the dry solids such as the active ingredient, the bulking agent, the binder, etc. and then wet them with a wetting agent such as water or alcohol; coagulate or granulate the wetted solids; continue the wet granulating until the required particle size of granules were uniformly obtained; after that, dry the granules. Then, mix the dried granules with a disintegrating agent, lubricant(s), antiadherent(s), etc.; tablet the mixture in a tableting machine; and optionally, coat the tablets with suitable coating powders.

What should be specially mentioned is the oral suspension. One advantage of this administration form is that patients need not to swallow solids, especially for elderly people, children or patients with injuries in the mouth or the throat, who may have difficulties in swallowing solids. The suspension is a two-phase system formed by dispersing solid grains into a liquid. For example, Crystal Form VI, Crystal Form VII, Crystal Form III, Crystal Form IV, Crystal Form V, Crystal Form VIII, Crystal Form Ie, Crystal Form VIIb or Crystal Form VIIIa of Dabrafenib of the present invention can keep its original solid form in water or an aqueous carrier of the suspension. The other ingredients in the oral suspension may include buffering agents, surface active agents, viscosity regulators, preservatives, antioxidants, colorants, flavoring agents and taste masking agents.

In addition, the present invention provides uses of Crystal Form VI, Crystal Form VII, Crystal Form III, Crystal Form IV, Crystal Form V, Crystal Form VIII, Crystal Form Ie, Crystal Form VIIb or Crystal Form VIIIa of Dabrafenib of the present invention in making drugs for inhibiting one or more Raf-family kinases.

In addition, the present invention provides a method of treating and/or preventing diseases associated with one or more Raf-family kinases, which comprising the administration of a therapeutically and/or preventively effective amount of Crystal Form VI, Crystal Form VII, Crystal Form III, Crystal Form IV, Crystal Form V, Crystal Form VIII, Crystal Form Ie, Crystal Form VIIb or Crystal Form VIIIa of Dabrafenib or the pharmaceutical composition containing Crystal Form VI, Crystal Form VII, Crystal Form III, Crystal Form IV, Crystal Form V, Crystal Form VIII, Crystal Form Ie, Crystal Form VIIb or Crystal Form VIIIa of Dabrafenib to the patients in need thereof. The patients include but not limited to mammals, such as humans.

The diseases associated with one or more Raf-family kinases include but not limited to sensitive tumors. The specific categories of sensitive tumors can refer to patent documents WO2009/137391 or U.S. Pat. No. 7,994,185. The "Sensitive Tumors" refers to the tumors which are sensitive to the treatment by kinase inhibitors, especially the tumors which are sensitive to the treatment by Raf inhibitor. The tumors associated with inappropriate activity of one or more Raf-family kinases, and particularly the tumors which exhibit the mutation of the Raf-family kinases, the overexpression of the Raf-family kinases, the mutation of the upstream activators of the Raf-family kinases, or the overexpression of the upstream activators of the Raf-family kinases, and are therefore sensitive to the treatment by Raf inhibitors are known in the prior art, including primary and metastatic tumors and cancers. The specific examples of sensitive tumors include but not limited to: Barret's adenocarcinoma; biliary tract carcinoma; breast cancer; cervical carcinoma; cholangiocarcinoma; central nervous system tumors including primary CNS tumors such as glioblastoma, astrocytoma and ependymal cell tumor, and secondary CNS tumors (i.e. metastatic tumor of central nervous system originates outside the central nervous system); colorectal cancer, including large intestinal colorectal cancer; gastric carcinoma; head and neck cancer including head and neck squamous cell carcinoma; hematological cancer including leukemia and lymphoma such as acute lymphocytic leukemia, acute myeloid leukemia, myelodysplastic syndrome, chronic myeloid leukemia, Hodgkin's lymphoma, non Hodgkin's lymphoma, megakaryocytic leukemia, multiple myeloma and erythroleukemia; hepatocellular carcinoma; lung cancer including small cell lung cancer and non-small cell lung cancer; ovarian cancer; endometrial carcinoma; pancreatic cancer; pituitary adenoma; prostate cancer; renal carcinoma; sarcoma; skin cancer including melanoma; and thyroid carcinoma.

DETAILED DESCRIPTION OF EMBODIMENTS

Figure 1:
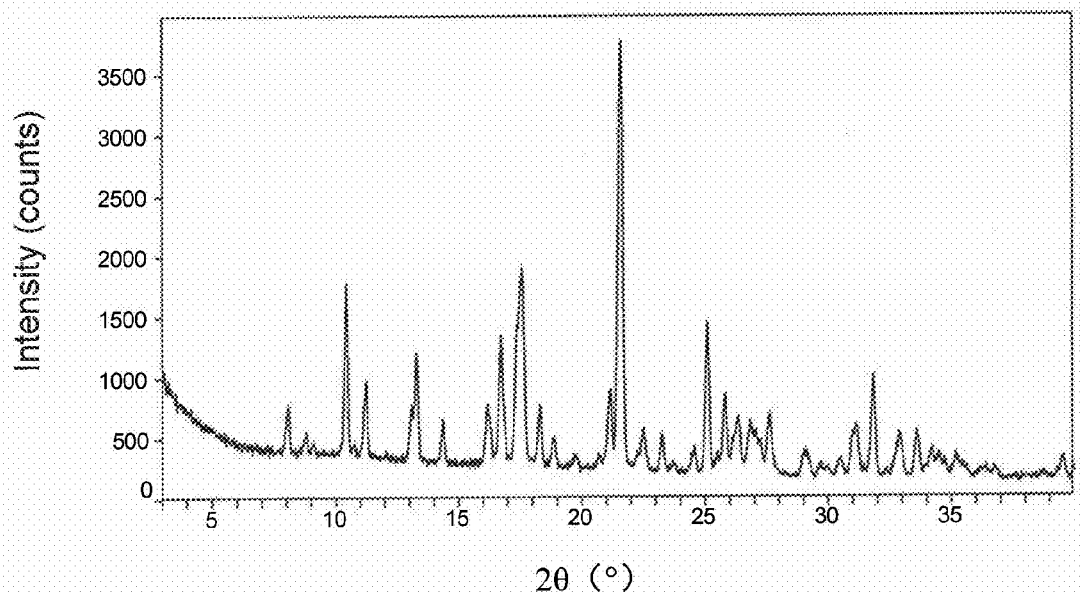
FIG. 1 is the X-ray powder diffraction pattern of Crystal Form VI of the present invention.

The present invention is defined with further reference to the following examples, which describe the preparation and usage of the crystal forms of the present invention in details. It is obvious to the scientists in this field that various changes in materials and methods may be embodied without deviating from the scope of the present invention. Instruments and methods used for data collection The instrument for X-ray powder diffraction (XPRD) is Bruker D8 Advance diffractometer, which uses the Cu Kα X-ray with 1.54 angstroms in wavelength, under the operation conditions of 40 kV and 40 mA, 0~20 goniometer, Mo monochromator and Lynxeye detector. Prior to use, the instrument is calibrated with the standard substance (generally corindon) attached. The acquisition software is Diffrac Plus XRD Commander. The sample is examined at room temperature, and placed on sample holder. The detailed testing conditions are as follows: range: 3~40°2θ; step size: 0.02°2θ; speed: 0.2 s/step.

Polarized Light Microscope (PLM) plots are collected from XP-500E polarized light microscope (by Shanghai Changfang Optical Instrument Co., Ltd). Place a small amount of powder sample on a slide glass, drip some mineral oil to disperse the powder sample, place the cover slip, then place the sample on the loading table of XP-500E polarized light microscope, choose the appropriate magnitude to observe the morphology of the sample and take pictures thereof.

The particle size distribution (PSD) plot is obtained using Microtrac S3500 laser diffraction particle size analyzer. The method parameters are as follows: flow velocity of the dispersant is 50%; the dispersant is water (added with 2% tween-80); the sample refractivity is 1.58; the laser source wavelength is 780 nm; and the integral mode is volume.

The Differential Scanning Calorimeter (DSC) data are collected by TA Instruments Q200 MDSC; the instrument control software is Thermal Advantage and the analysis software is Universal Analysis. Generally, take 1~10 mg of the sample and place it in an uncovered (unless otherwise specified) aluminum pan and under the protection of 50 mL/min dry $N_2$, heat the sample from room temperature to 250° C. at the heating rate of 10° C./min; and heat absorption by and heat release from the sample during the course are recorded by TA software simultaneously. In the present application, the melting point is reported based on DSC onset temperature.

The thermogravimetric analysis (TGA) data are collected by TA Instruments Q500 TGA; the instrument control software is Thermal Advantage and the analysis software is Universal Analysis. Generally, take 5~15 mg sample and place it in a platinum pan, adopt the segmental high-resolution testing mode, and under the protection of 50 mL/min dry $N_2$, heat the sample from room temperature to 300° C. at the heating rate of 10° C./min, the weight changes of the sample during the course are recorded by TA software simultaneously.

The nuclear magnetic resonance hydrogen spectrum ($^1$HNMR) data are collected by Bruker Avance II DMX 400M HZ NMR spectrometer. Weigh 1~5 mg of the sample, dissolve it with 0.5 mL DMSO-d6 to get a 2 mg/mL-10 mg/mL solution.

The dynamic vapor sorption analysis (DVS) data are collected by TA Instruments Q5000 TGA; the instrument control software is Thermal Advantage and the analysis software is Universal Analysis. Generally, take 1~10 mg of the sample and place it in a platinum pan, and the weight changes of the sample are recorded during the course of the relative humidity changing from 0% to 80% and then to 0%. According to the specifics of the samples, different adsorption and desorption steps may be used.

Preparation Example 1

The preparation of the Known Crystal Form 1: Refer to the preparation method described in example 58a of patent document WO2009/137391A2 or U.S. Pat. No. 7,994,185B2, with the details as follows:

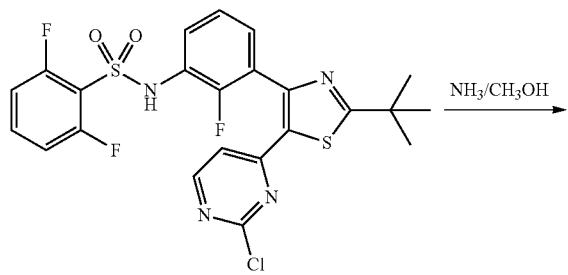

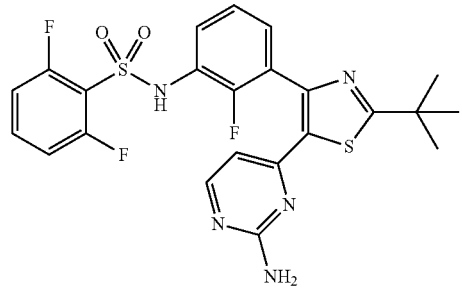

Add N-{3-[5-(2-chloro-4-pyrimidinyl)-2-(1,1-dimethylethyl)-1,3-thiazol-4-yl]-2-fluorophenyl}-2,6-difluorobenzenesulfonamide (196 mg, 0.364 mmol) and 7M methanol solution of ammonia (8 ml, 56 mmol) into a 25 mL autoclave, heat to 90° C. and react for 24 h; when the TLC shows the raw material is completely reacted, cool the above reaction system to room temperature, filter to get N-{3-[5-(2-amino-4-pyrimidinyl)-2-(1,1-dimethylethyl)-1,3-thiazol-4-yl]-2-fluorophenyl}-2,6-difluorobenzenesulfonamide (i.e. Dabrafenib). $^1$H-NMR (400 MHz, DMSO-d6) δppm 10.83 (s, 1H), 7.93 (d, J=5.2 Hz, 1H), 7.55-7.70 (m, 1H), 7.35-7.43 (m, 1H), 7.31 (t, J=6.3 Hz, 1H), 7.14-7.27 (m, 3H), 6.70 (s, 2H), 5.79 (d, J=5.13 Hz, 1H), 1.35 (s, 9H).

Figure 25:
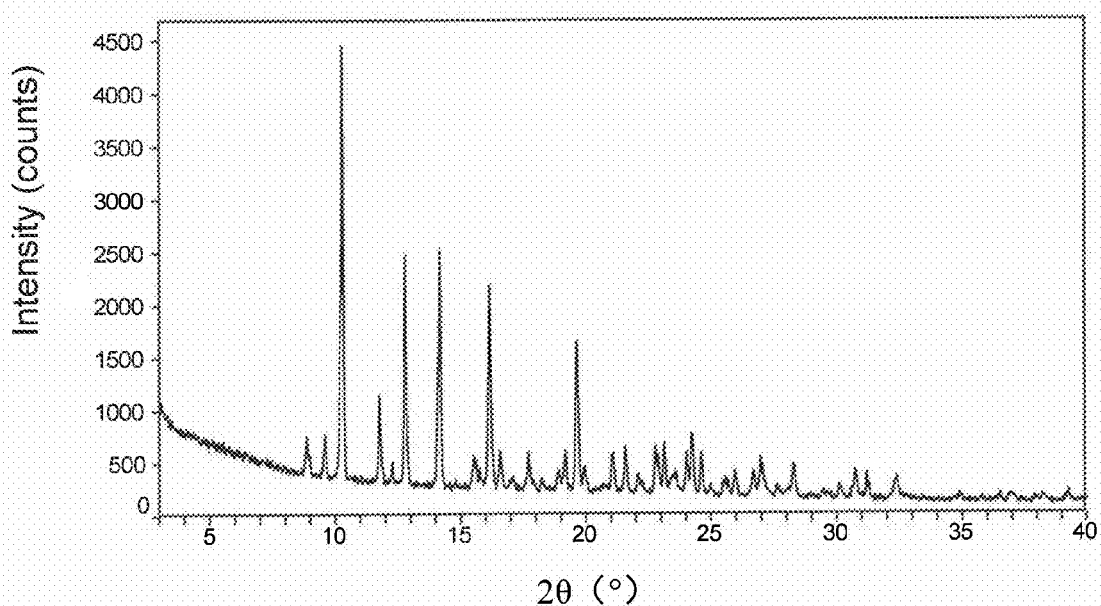
FIG. 25 is the X-ray powder diffraction pattern of the Known Crystal Form 1 prepared by the method described in example 58a of patent document WO2009/137391A2 or U.S. Pat. No. 7,994,185B2.

The XPRD pattern is as shown in FIG. 25 and is substantially the same as that of the Known Crystal Form 1 of Dabrafenib prepared in example 58a of patent document U.S. Pat. No. 7,994,185B2.

Figure 26:
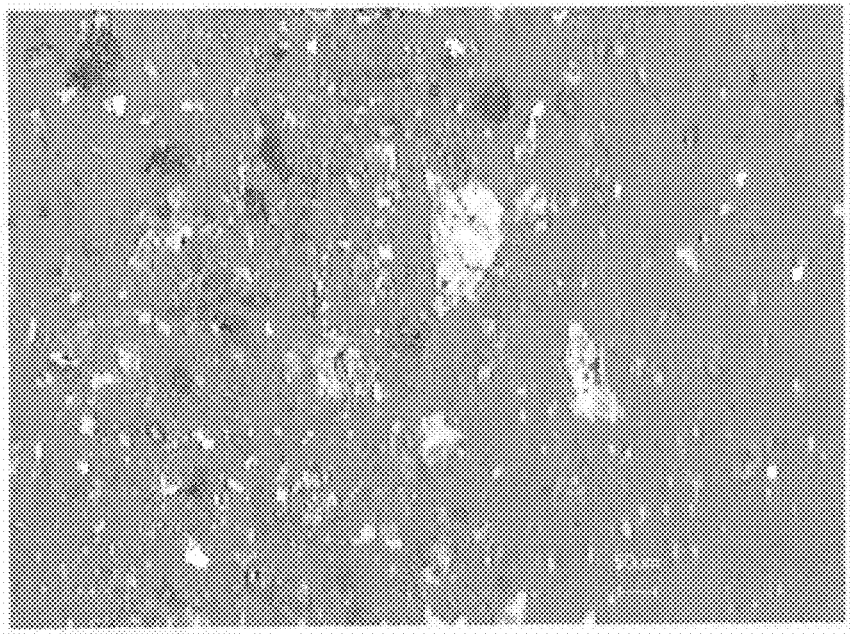
FIG. 26 is the PLM plot of the Known Crystal Form 1 prepared by the method described in example 58a of patent document WO2009/137391A2 or U.S. Pat. No. 7,994,185B2.

The PLM plot is as shown in FIG. 26. It shows small block-shaped crystals.

PSD shows: D10, D50 and D90 are 40 μm, 104 μm and 151 μm, respectively.

Figure 27:
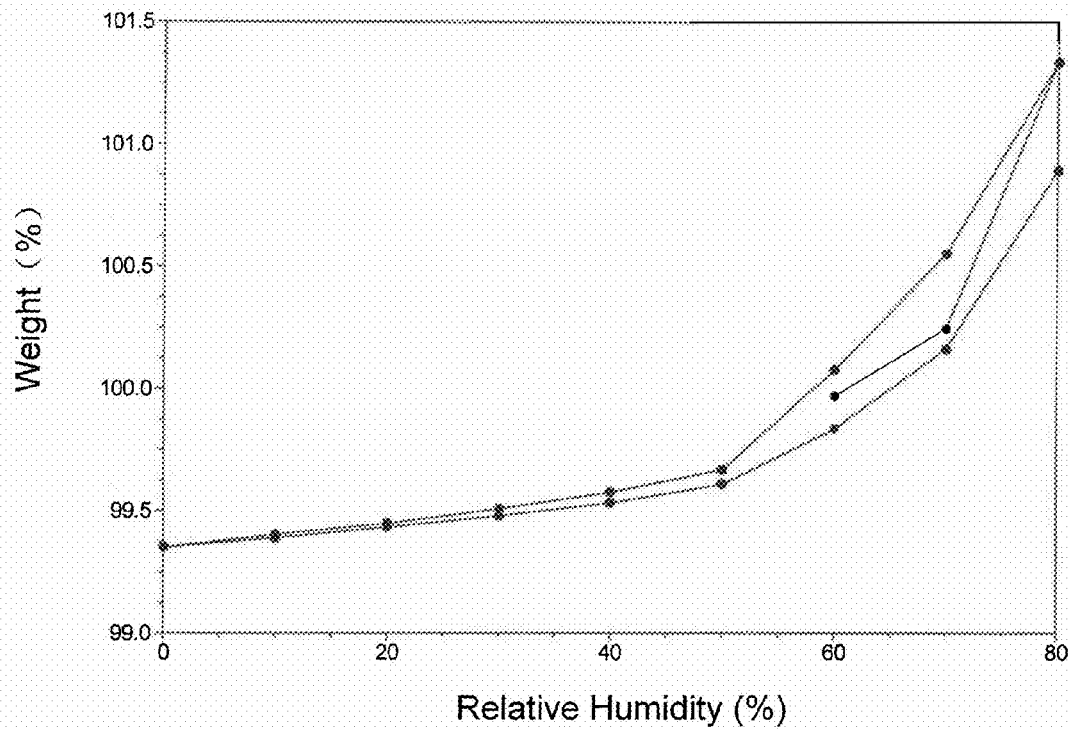
FIG. 27 is the dynamic vapor sorption isotherm of the Known Crystal Form 1 prepared by the method described in example 58a of patent document WO2009/137391A2 or U.S. Pat. No. 7,994,185B2.

The dynamic vapor sorption isothermal is as shown in FIG. 27. It shows: the weight change is 1.9% between 20% RH~80% RH.

Preparation Example 2

The Known Crystal Form 2 may be prepared by the following method: Refer to the preparation method described in example 58b of patent document WO2009/137391A2 or U.S. Pat. No. 7,994,185B2, with the details as follows: At room temperature, add 19.6 mg of the Known Crystal Form 1 prepared by the method described in example 58a of patent document WO2009/137391A2 or U.S. Pat. No. 7,994,185B2 and 500 μL of ethyl acetate in a 2 mL-vial, circulate the slurry for 48 h at 0~40° C., then cool to room temperature, filter to get the solids.

Figure 22:
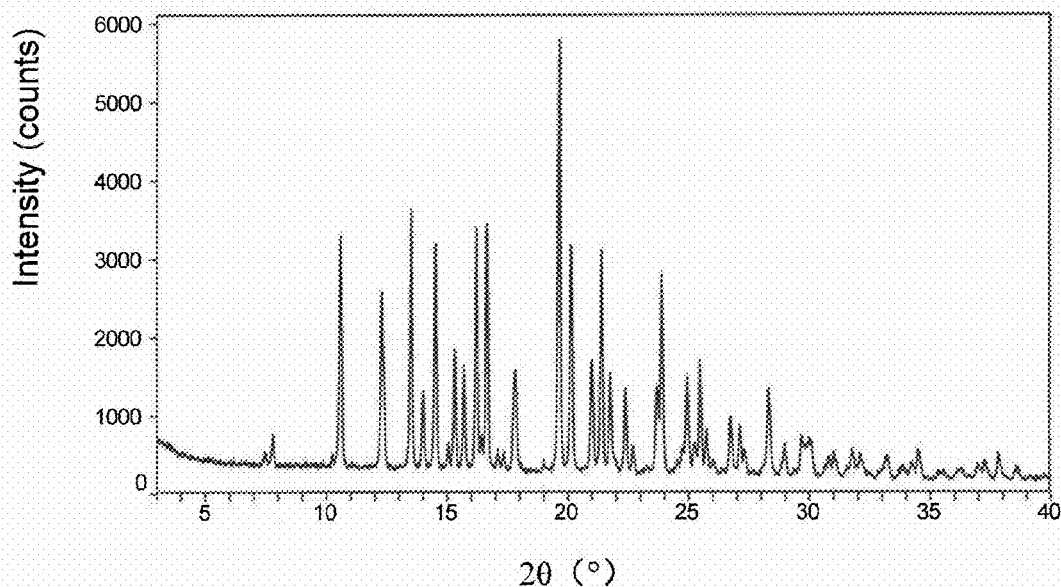
FIG. 22 is the X-ray powder diffraction pattern of the Known Crystal Form 2 prepared by the method described in example 58b of patent document WO2009/137391A2 or U.S. Pat. No. 7,994,185B2.

The XPRD pattern is shown in FIG. 22 and is substantially the same as that of the Known Crystal Form 2 of Dabrafenib disclosed by patent document WO2012/148588A2.

Figure 23:
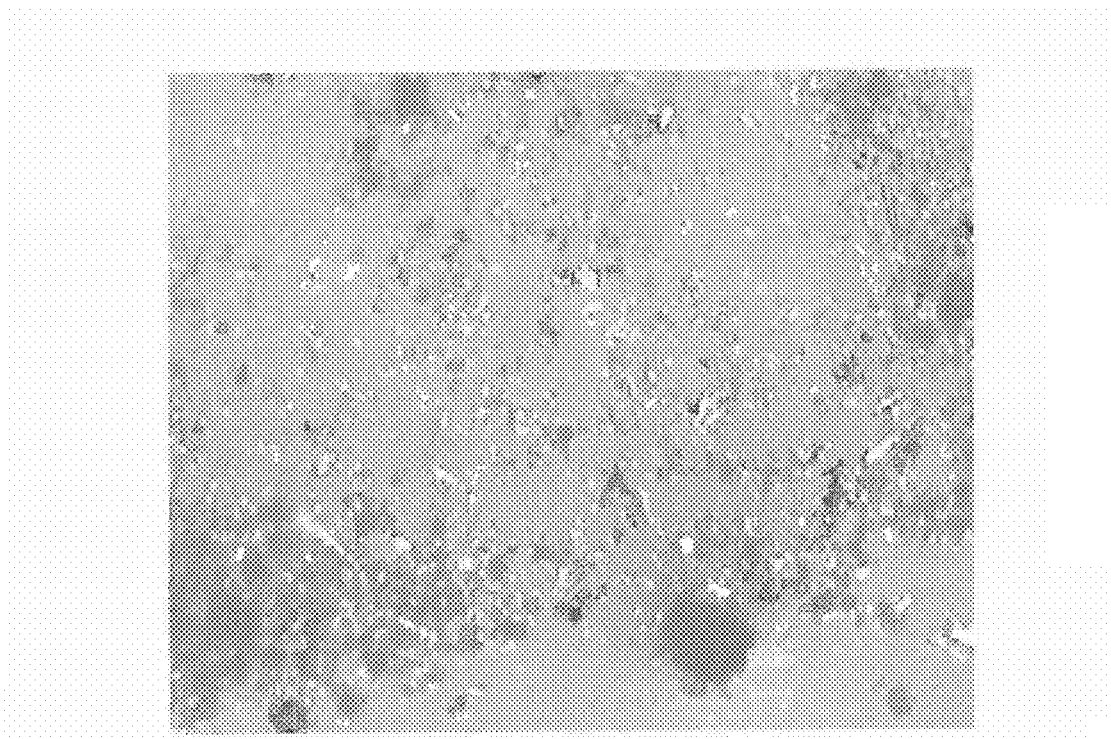
FIG. 23 is the PLM plot of the Known Crystal Form 2 prepared by the method described in example 58b of patent document WO2009/137391A2 or U.S. Pat. No. 7,994,185B2.

The PLM plot is shown in FIG. 23. It shows small block-shaped crystals.

PSD shows: D10, D50 and D90 are 16 μm, 36 μm and 74 μm, respectively.

Figure 24:
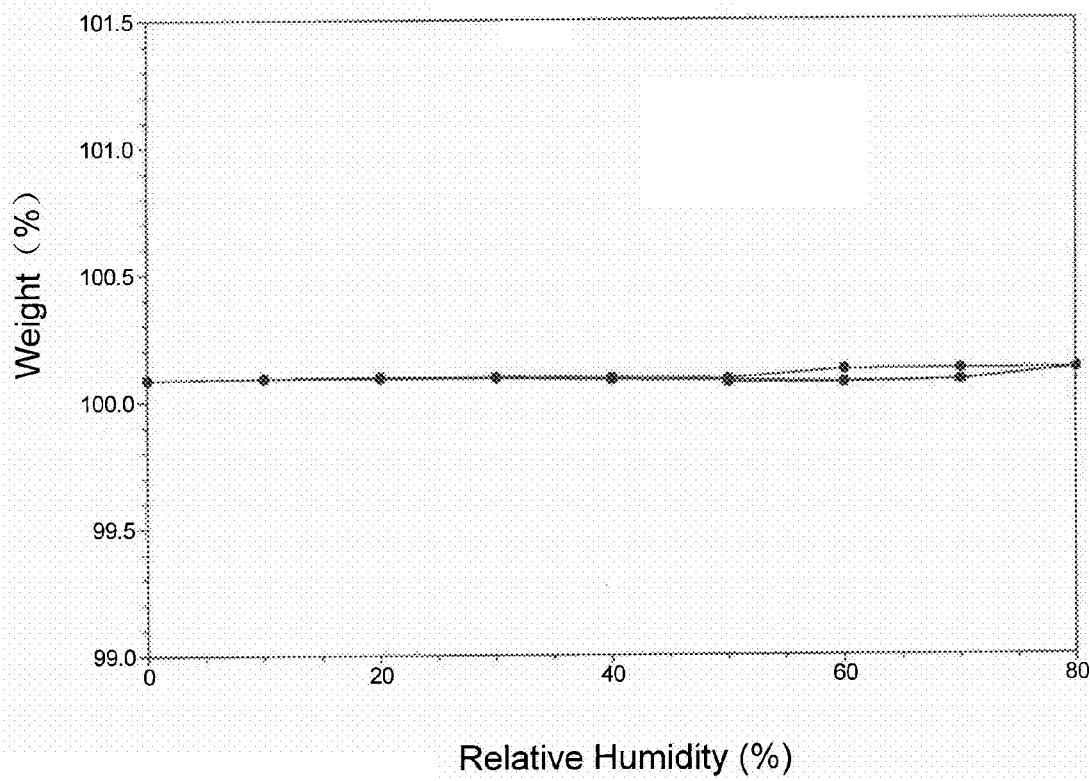
FIG. 24 is the dynamic vapor sorption isothermal of the Known Crystal Form 2 prepared by the method described in example 58b of patent document WO2009/137391A2 or U.S. Pat. No. 7,994,185B2.

The dynamic vapor sorption isotherm is shown in FIG. 24. It shows: the weight change is 0.03% between 20% RH~80% RH.

Preparation Example 3

Preparation of the amorphous form: Take 10 mg of the Known Crystal Form 2 of Dabrafenib and place it in a 5 mL-vial, add 4 mL of anhydrous ethanol, take the ultrasonic treatment until the solution becomes clear; then remove the solvent completely by the rotary evaporation at 40° C. to get an oil.

Unless otherwise specified, all the following examples are operated at room temperature.

In the examples, the ultrasonic operation facilitates the dissolution of the sample. Place the container filled with the suspension of the sample in the ultrasonic cleaner and treat it for 1~30 min at the working power of 20 Khz~40 Khz. Generally, keep the ultrasonic treatment for 5 min at the ultrasonic power of 40 Khz.

In the examples, the operation of the rotary evaporation is as follows: At the temperature between room temperature and the boiling point of the solvent (preferably 30~50° C.), and under the pressure below the atmospheric pressure (preferably below 0.08 MPa), the operation is carried out at the rotation speed of 10~180 rpm (preferably 50~100 rpm).

Example 1

Take 5.0 mg the Known Crystal Form 2 of Dabrafenib and place it into a 250 mL round-bottom flask, add 200 mL of water, use the ultrasonic treatment to get a suspension (wherein the quantity of Dabrafenib is 20 times of its solubility in water at room temperature), stir it for 7 days at room temperature, centrifugate, and then dry it in a vacuum oven for 24 h at 40° C. to get Crystal Form VI of the present invention. The product is 3.4 mg and the yield is 68%.

The XPRD pattern is as shown in FIG. 1.

Figure 2:
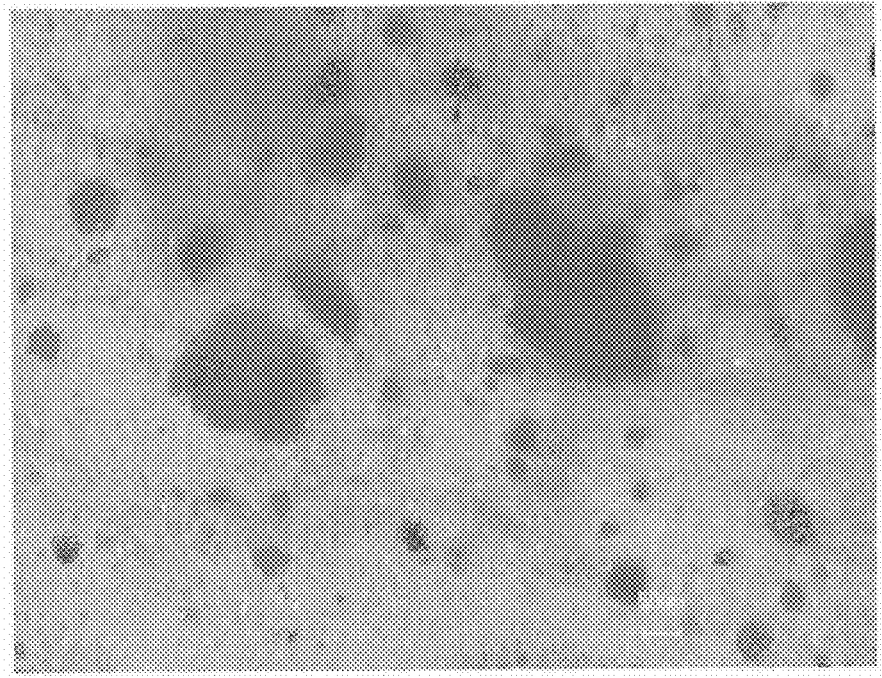
FIG. 2 is the PLM plot of Crystal Form VI of the present invention.

The PLM plot is as shown in FIG. 2. It shows fine crystals.

PSD shows: D10, D50 and D90 are 7 pun, 18 μm and 40 μm, respectively.

Figure 3:
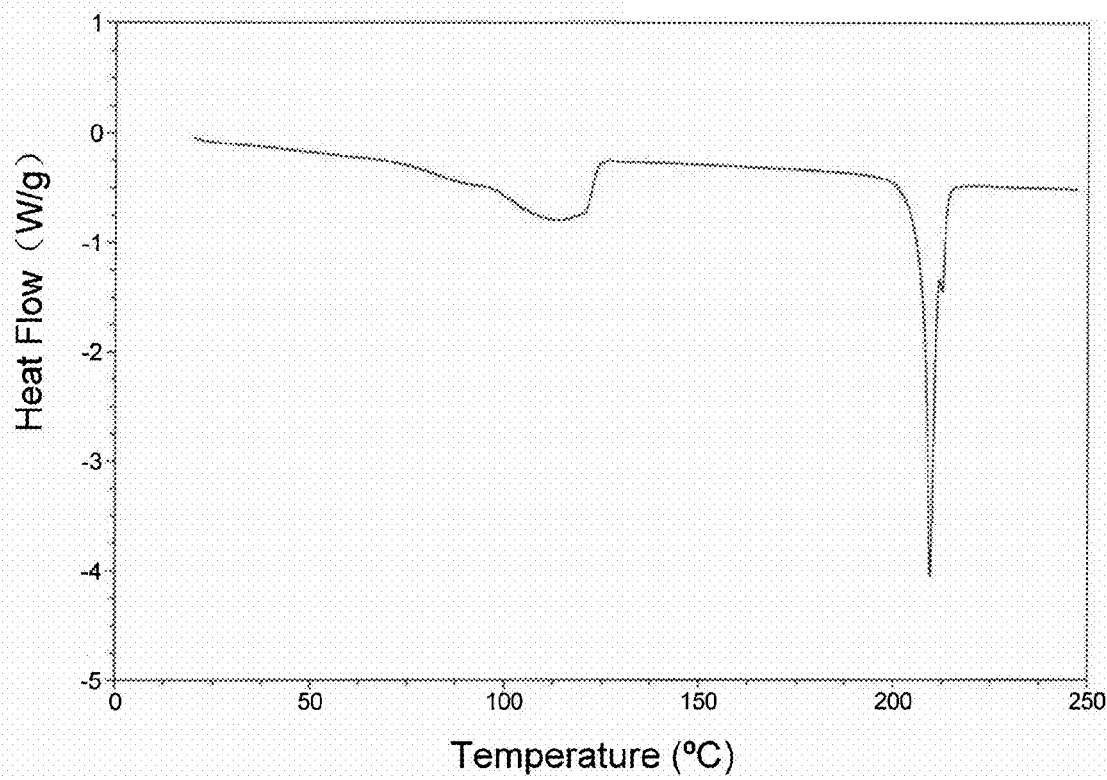
FIG. 3 is the DSC thermogram of Crystal Form VI of the present invention.

The DSC thermogram is as shown in FIG. 3. It shows: Crystal Form VI has a wide and large endothermic peak (the solvent peak) at 64~128° C. and the melting point of the dehydrated sample is 206° C.

Figure 4:
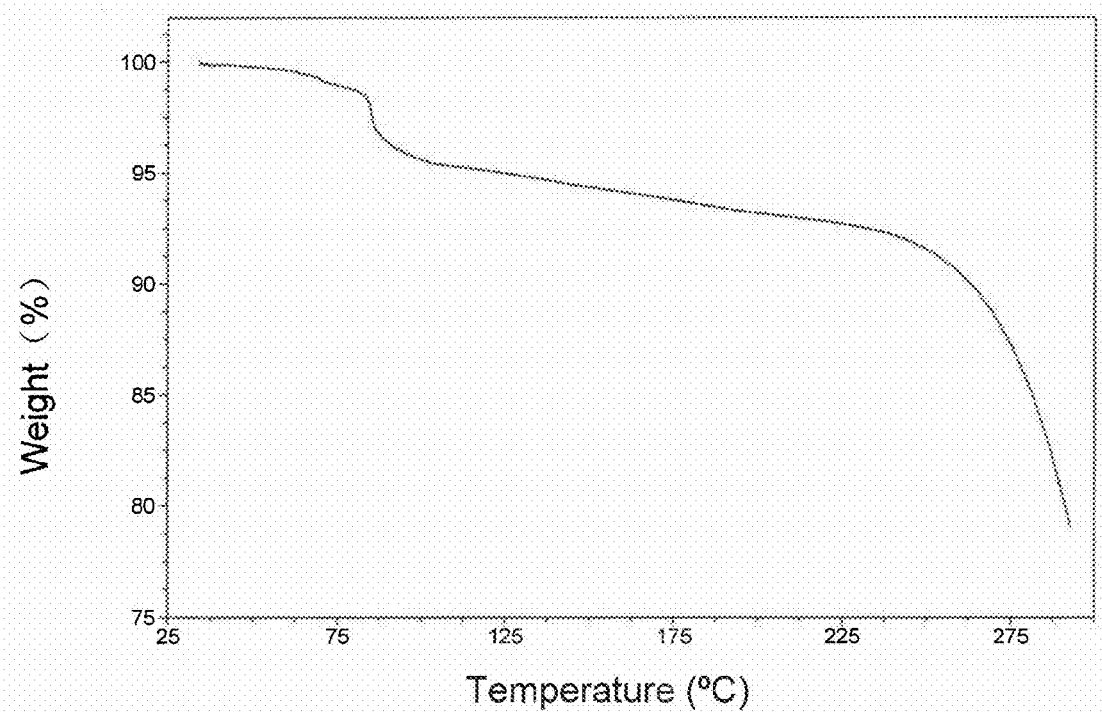
FIG. 4 is the TGA thermogram of Crystal Form VI of the present invention.

The TGA thermogram is as shown in FIG. 4. It shows the weight loss of Crystal Form VI prior to 112° C. is about 3.8% and the decomposition temperature is 271° C. Based on the weight loss of TGA, it is confirmed that Crystal Form VI is monohydrate.

Figure 5:
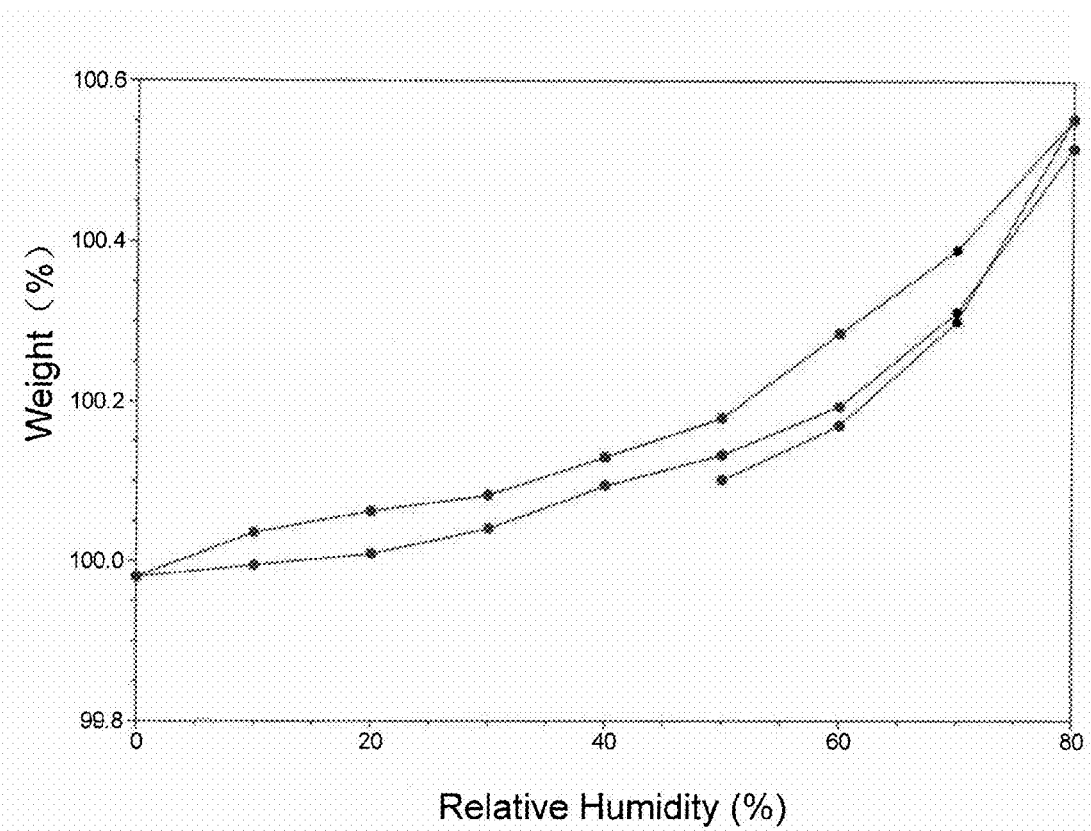
FIG. 5 is the dynamic vapor sorption isothermal of Crystal Form VI of the present invention.

The dynamic vapor sorption isotherm is as shown in FIG. 5. It shows the weight change is 0.5% between 20% RH~80% RH.

The above test results show that Crystal Form VI is very stable at high temperature and not hygroscopic.

Example 2

Figure 6:
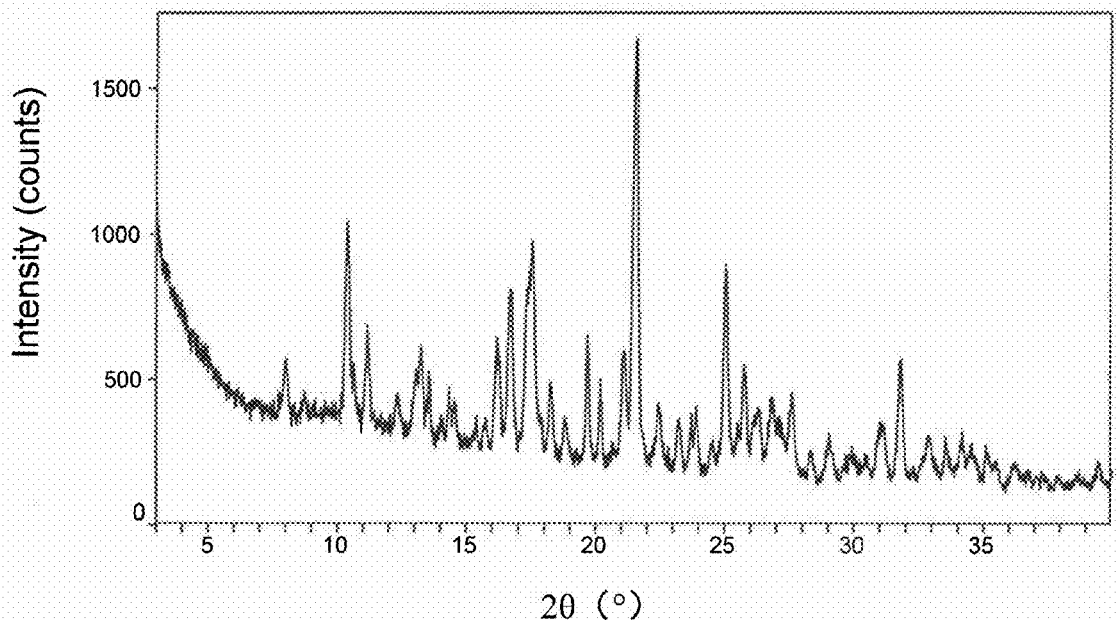
FIG. 6 is another X-ray powder diffraction pattern of Crystal Form VI of the present invention.

Take 8.4 mg of the Known Crystal Form 2 of Dabrafenib and place it into a 5 mL vial, add 0.3 mL aqueous methanol solution (wherein the water volume content is 0.01%), use the ultrasonic treatment to get a suspension (wherein the quantity of Dabrafenib is 1.5 times of its solubility in the mentioned aqueous methanol solution at room temperature), stir it for 3 days at room temperature, centrifugate, and then dry it in a vacuum oven for 24 h at room temperature to get Crystal Form VI of the present invention. The product is 6.7 mg and the yield is 80%. The XPRD pattern is as shown in FIG. 6 and is substantially same as FIG. 1.

Example 3

Take 7.9 mg of the Known Crystal Form 2 of Dabrafenib and place it into a 5 mL-vial, add 0.5 mL of aqueous ethanol solution (wherein the water volume content is 80%), use the ultrasonic treatment to get a suspension (wherein the quantity of Dabrafenib is 3 times of its solubility in the mentioned aqueous ethanol solution at room temperature), stir it for 3 days at 40° C., centrifugate, and then dry it in vacuum for 24 h at room temperature to get Crystal Form VI of the present invention. The product is 6.1 mg and the yield is 77%. Its XPRD pattern is substantially the same as FIG. 1.

Example 4

Take 6.7 mg of the Known Crystal Form 2 of Dabrafenib and place it into a 5 mL-vial, add 1.0 mL of aqueous isopropanol solution (wherein the water volume content is 99.99%), use the ultrasonic treatment to get a suspension (wherein the quantity of Dabrafenib is 10 times of its solubility in the mentioned aqueous isopropanol solution at room temperature), stir it for 7 days at room temperature, centrifugate, and then dry it in a vacuum oven for 24 h at 40° C. to get Crystal Form VI of the present invention. The product is 4.9 mg and the yield is 73%. Its XPRD pattern is substantially the same as FIG. 1.

Example 5

Take 4.1 mg of the Known Crystal Form 1 of Dabrafenib and place it into a 5 mL-vial, add 0.35 mL of water-saturated n-butanol solution, use the ultrasonic treatment to get a suspension (wherein the quantity of Dabrafenib is 20 times of its solubility in the water-saturated n-butanol solution at 60° C.), stir it for 7 days at 60° C., centrifugate, and then dry it in a vacuum oven for 48 h at 60° C. to get Crystal Form VI of the present invention. The product is 2.9 mg and the yield is 71%. Its XPRD pattern is substantially the same as FIG. 1.

Example 6

Take 6.9 mg of the Known Crystal Form 2 of Dabrafenib and place it into a 5 mL-vial, add 4.0 mL of water-saturated nitromethane solution, use the ultrasonic treatment to get a suspension (wherein the quantity of Dabrafenib is 1.5 times of its solubility in the water-saturated nitromethane solution at 60° C.), stir it for 7 days at 60° C., centrifugate, and then dry it in vacuum for 48 h at 60° C. to get Crystal Form VI of the present invention. The product is 4.0 mg and the yield is 58%. Its XPRD pattern is substantially the same as FIG. 1.

Example 7

Take 4.1 mg of the amorphous form of Dabrafenib and place it into a 5 mL-vial, add 0.1 mL of aqueous acetone solution (wherein the water volume content is 0.1%), use the ultrasonic treatment to get a suspension (wherein the quantity of Dabrafenib is 1.5 times of its solubility in the mentioned aqueous acetone solution at room temperature), stir it for 14 days at room temperature, centrifugate, and then dry it in a vacuum oven for 2 h at room temperature to get Crystal Form VI of the present invention. The product is 3.8 mg and the yield is 93%. Its XPRD pattern is substantially the same as FIG. 1.

Example 8

Take 9.4 mg of the Known Crystal Form 2 of Dabrafenib and place it into a 5 mL-vial, add 0.3 mL of water-saturated butanone solution, use the ultrasonic treatment to get a suspension (wherein the quantity of Dabrafenib is 1.5 times of its solubility in the water-saturated butanone solution at room temperature), stir it for 7 days at room temperature, centrifugate, and then dry it in a vacuum oven for 2 h at room temperature to get Crystal Form VI of the present invention. The product is 6.8 mg and the yield is 72%. Its XPRD pattern is substantially the same as FIG. 1.

Example 9

Take 15.3 mg of the Known Crystal Form 2 of Dabrafenib and place it into a 5 mL-vial, add 0.3 mL of water-saturated ethyl ether solution, use the ultrasonic treatment to get a suspension (wherein the quantity of Dabrafenib is 10 times of its solubility in the water-saturated ethyl ether solution at room temperature), stir it for 14 days at room temperature, centrifugate, and then dry it in a vacuum oven for 2 h at room temperature to get Crystal Form VI of the present invention. The product is 12.7 mg and the yield is 83%. Its XPRD pattern is substantially the same as FIG. 1.

Example 10

Take 18.9 mg of the amorphous form of Dabrafenib and place it into a 5 mL-vial, add 0.5 mL of water-saturated ethyl acetate solution, use the ultrasonic treatment to get a suspension (wherein the quantity of Dabrafenib is 2 times of its solubility in the water-saturated ethyl acetate solution at room temperature), stir it for 7 days at 40° C., centrifugate, and then dry it in a vacuum oven for 24 h at room temperature to get Crystal Form VI of the present invention. The product is 17.7 mg and the yield is 94%. Its XPRD pattern is substantially the same as FIG. 1.

Example 11

Take 1.3 mg of the Known Crystal Form 2 of Dabrafenib and place it into a 5 mL-vial, add 0.5 mL of water-saturated methyl tert-butyl ether solution, use the ultrasonic treatment to get a suspension (wherein the quantity of Dabrafenib is 20 times of its solubility in the water-saturated methyl tert-butyl ether solution at room temperature), stir it for 14 days at room temperature, centrifugate, and then dry it in vacuum for 2 h at room temperature to get Crystal Form VI of the present invention. The product is 0.8 mg and the yield is 62%. Its XPRD pattern is substantially the same as FIG. 1.

Example 12

Take 10.3 mg of the Known Crystal Form 2 of Dabrafenib and place it into a 5 mL-vial, add 0.4 mL of water-saturated isopropyl acetate solution, use the ultrasonic treatment to get a suspension (wherein the quantity of Dabrafenib is 1.5 times of its solubility in the water-saturated isopropyl acetate solution at room temperature), stir it for 3 days at room temperature, centrifugate, and then dry it in a vacuum oven for 24 h at 40° C. to get Crystal Form VI of the present invention. The product is 6.8 mg and the yield is 66%. Its XPRD pattern is substantially the same as FIG. 1.

Example 13

Take 10.3 mg of the Known Crystal Form 2 of Dabrafenib and place it into a 5 mL-vial, add 0.1 mL of aqueous tetrahydrofuran solution (wherein the water volume content is 0.1%), use the ultrasonic treatment to get a suspension (wherein the quantity of Dabrafenib is 1.5 times of its solubility in the mentioned aqueous tetrahydrofuran solution at room temperature), stir it for 3 days at room temperature, centrifugate, and then dry it in a vacuum oven for 24 h at 40° C. to get Crystal Form VI of the present invention. The product is 6.8 mg and the yield is 66%. Its XPRD pattern is substantially the same as FIG. 1.

Example 14

Take 10.3 mg of the Known Crystal Form 1 of Dabrafenib and place it into a 5 mL-vial, add 0.8 mL of aqueous acetonitrile solution (wherein the water volume content is 20%), use the ultrasonic treatment to get a suspension (wherein the quantity of Dabrafenib is 5 times of its solubility in the mentioned aqueous acetonitrile solution at room temperature), stir it for 3 days at room temperature, centrifugate, and then dry it in a vacuum oven for 24 h at 40° C. to get Crystal Form VI of the present invention. The product is 6.8 mg and the yield is 66%. Its XPRD pattern is substantially the same as FIG. 1.

Example 15

Take 1.0 mg of the Known Crystal Form 2 of Dabrafenib and place it into a 5 mL-vial, add 4.0 mL water-saturated n-hexane solution, use the ultrasonic treatment to get a suspension (wherein the quantity of Dabrafenib is 20 times of its solubility in the water-saturated n-hexane solution at room temperature), stir it for 14 days at 40° C., centrifugate, and then dry it in a vacuum oven for 24 h at room temperature to get Crystal Form VI of the present invention. The product is 0.6 mg and the yield is 60%. Its XPRD pattern is substantially the same as FIG. 1.

Example 16

Take 1.2 mg of the Known Crystal Form 1 of Dabrafenib and place it into a 5 mL vial, add 5.0 mL of water-saturated n-heptane solution, use the ultrasonic treatment to get a suspension (wherein the quantity of Dabrafenib is 20 times of its solubility in the water-saturated n-heptane solution at room temperature), stir it for 7 days at room temperature, centrifugate, and then dry it in a vacuum oven for 24 h at room temperature to get Crystal Form VI of the present invention. The product is 0.5 mg and the yield is 42%. Its XPRD pattern is substantially the same as FIG. 1.

Example 17

Figure 7:
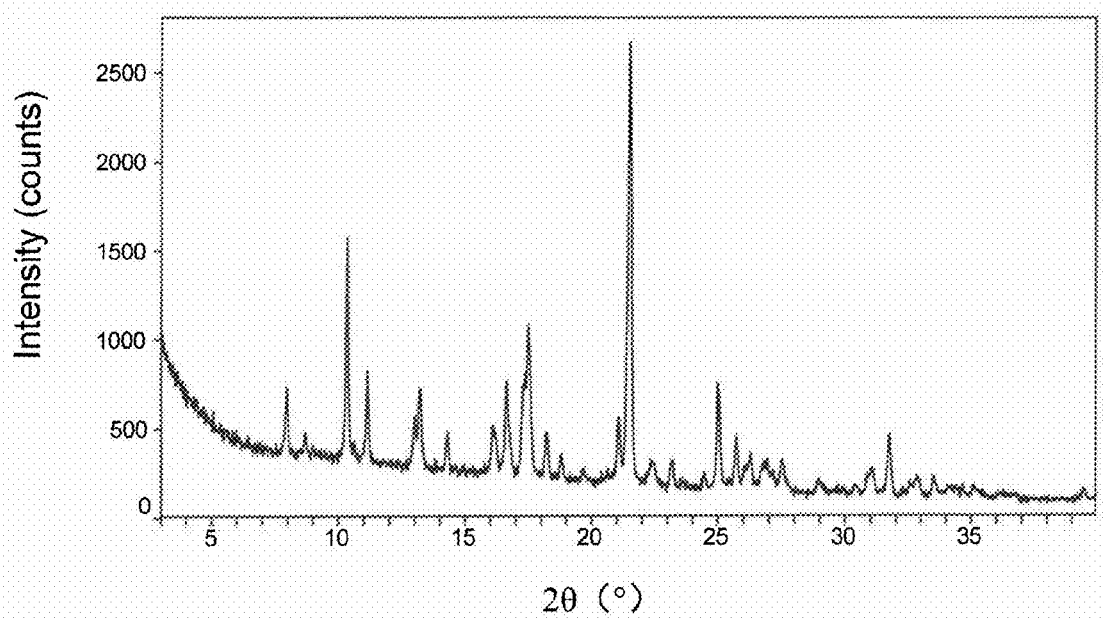
FIG. 7 is another X-ray powder diffraction pattern of Crystal Form VI of the present invention.

Take 4.8 mg of the Known Crystal Form 2 of Dabrafenib and place it into a 20 mL-vial, add 1.6 mL aqueous isopropanol solution (wherein the water volume content is 0.1%), use the ultrasonic treatment until the solution becomes clear, then filter it with 0.45 μm organic filter membrane, place the uncovered vial filled with the filtrate in a sealed 100 mL-space filled with 15 mL of mineral ether—for 3 weeks, centrifugate until after mineral ether diffused into the isopropanol solution and a great amount of solids emerge, dry it in a vacuum oven for 24 h at 40° C. to get Crystal Form VI of the present invention. The product is 4.0 mg and the yield is 83%. The XPRD pattern is as shown in FIG. 7 and substantially the same as FIG. 1.

Example 18

Take 0.4 mg of the amorphous form of Dabrafenib and place it into a 20 mL-vial, add 4.0 mL of aqueous isopropanol solution (wherein the water volume content is 10%), use the ultrasonic treatment until the solution becomes clear, then filter it with 0.45 μm organic filter membrane, place the uncovered vial filled with the filtrate in a sealed 100 mL space filled with 15 mL of isopropyl ether—for 1 week, centrifugate until after isopropyl ether diffused into the isopropanol solution and a great amount of solids emerge, dry it in a vacuum oven for 24 h at 40° C. to get Crystal Form VI of the present invention. The product is 0.1 mg and the yield is 25%. Its XPRD pattern is substantially same as FIG. 1.

Example 19

Take 2.5 mg of the Known Crystal Form 2 of Dabrafenib and place it into a 20 mL-vial, add 0.5 mL of aqueous nitromethane solution (wherein the water volume content is 1%), use the ultrasonic treatment until the solution becomes clear, then filter it with 0.45 μm organic filter membrane, place the uncovered vial filled with the filtrate in a sealed 100 mL-space filled with 15 mL of isopropyl ether—for 3 weeks, centrifugate until after isopropyl ether diffused into the nitromethane solution and a great amount of solids emerge, dry it in a vacuum oven for 48 h at 40° C. to get Crystal Form VI of the present invention. The product is 1.9 mg and the yield is 76%. Its XPRD pattern is substantially the same as FIG. 1.

Example 20

Take 0.5 mg of the Known Crystal Form 1 of Dabrafenib and place it into a 20 mL-vial, add 5 mL of aqueous nitromethane solution (wherein the water volume content is 0.01%), use the ultrasonic treatment until the solution becomes clear, then filter it with 0.45 μm organic filter membrane, place the uncovered vial filled with the filtrate in a sealed 100 mL space filled with 15 mL of mineral ether—for 3 weeks, centrifugate until after mineral ether diffused into the nitromethane solution and a great amount of solids emerge, dry it in a vacuum oven for 24 h at 40° C. to get Crystal Form VI of the present invention. The product is 0.2 mg and the yield is 40%. Its XPRD pattern is substantially the same as FIG. 1.

Example 21

At room temperature, take 9.5 mg of the Known Crystal Form 2 of Dabrafenib and place it into a 20 mL-vial, add 1.5 mL of methanol, use the ultrasonic treatment for 5 mins to dissolve the sample completely (wherein the quantity of Dabrafenib is 0.5 times of its solubility in methanol at room temperature), in which add 0.15 mL of water dropwise to get white solid immediately, stir it for 7 days at room temperature, centrifugate, and dry it in a vacuum oven for 24 h at 40° C. to get Crystal Form VI of the present invention. The product is 9.0 mg and the yield is 95%. Its XPRD pattern is substantially the same as FIG. 1.

Example 22

At room temperature, take 0.6 mg of the Known Crystal Form 1 of Dabrafenib and place it into a 20 mL-vial, add 5 mL of n-butanol, use the ultrasonic treatment for 5 min, then filter it with 0.45 μm organic filter membrane to get the filtrate (wherein the quantity of Dabrafenib is 1 time of its solubility in n-butanol at room temperature), in which dropwise add 2.5 mL of n-hexane phase of the water-saturated n-hexane solution to get white solid immediately, stir it for 10 days at room temperature, centrifugate, and dry it in a vacuum oven for 24 h at 40° C. to get Crystal Form VI of the present invention. The product is 0.4 mg and the yield is 67%. Its XPRD pattern is substantially the same as FIG. 1.

Example 23

At room temperature, take 19.0 mg of the Known Crystal Form 2 of Dabrafenib and place it into a 100 mL-round-bottomed flask, add 1 mL of ethyl acetate, use the ultrasonic treatment for 5 min to dissolve the sample completely (wherein the quantity of Dabrafenib is 1 time of its solubility in ethyl acetate at room temperature), in which dropwise add 50 mL of n-heptane phase of the water-saturated n-heptane solution to get white solid immediately, stir it for 10 days at room temperature, centrifugate, and dry it in a vacuum oven for 24 h at 40° C. to get Crystal Form VI of the present invention. The product is 15.1 mg and the yield is 79%. Its XPRD pattern is substantially the same as FIG. 1.

Example 24

At room temperature, take 3.2 mg of the amorphous form of Dabrafenib and place it into a 300 mL-round-bottomed flask, add 2.5 mL of isopropyl acetate, use the ultrasonic treatment for 5 min to dissolve the sample completely (wherein the quantity of Dabrafenib is 0.1 times of its solubility in isopropyl acetate at room temperature), in which add 250 mL of cyclohexane phase of the water-saturated cyclohexane solution dropwise to get white solid immediately, stir it for 10 days at 40° C., centrifugate, and dry it in vacuum for 24 h at 40° C. to get Crystal Form VI of the present invention. The product is 0.8 mg and the yield is 25%. Its XPRD pattern is substantially the same as FIG. 1.

Example 25

At room temperature, take 4.2 mg of the Known Crystal Form 2 of Dabrafenib and place it into a 5 mL-vial, add 1 mL of ethyl ether, use the ultrasonic treatment for 5 min to dissolve the sample completely (wherein the quantity of Dabrafenib is 1 time of its solubility in ethyl ether at room temperature), in which add 0.5 mL of methyl cyclohexane phase of the water-saturated methyl cyclohexane solution dropwise to get white solid immediately, stir it for 7 days at room temperature, centrifugate, and dry it in vacuum for 24 h at 40° C. to get Crystal Form VI of the present invention. The product is 3.3 mg and the yield is 78%. Its XPRD pattern is substantially the same as FIG. 1.

Example 26

At room temperature, take 5.2 mg of the Known Crystal Form 2 of Dabrafenib and place it into a 5 mL-vial, add 1 mL of methyl tert-butyl ether, use the ultrasonic treatment for 5 min to dissolve the sample completely (wherein the quantity of Dabrafenib is 1 time of its solubility in methyl tert-butyl ether at room temperature), in which add 0.5 mL of methyl cyclohexane phase of the water-saturated methyl cyclohexane solution dropwise to get white solid immediately, stir it for 7 days at room temperature, centrifugate, and dry it in vacuum for 24 h at 40° C. to get Crystal Form VI of the present invention. The product is 5.0 mg and the yield is 96%. Its XPRD pattern is substantially the same as FIG. 1.

Example 27

At room temperature, take 23.2 mg of the Known Crystal Form 1 of Dabrafenib and place it into a 5 mL-vial, add 1 mL of acetone, use the ultrasonic treatment for 5 mins to dissolve the sample completely (wherein the quantity of Dabrafenib is 1 time of its solubility in acetone at room temperature), in which add 0.1 mL of water dropwise to get white solid immediately, stir it for 3 days at room temperature, centrifugate, and dry it in a vacuum oven for 24 h at 40° C. to get Crystal Form VI of the present invention. The product is 19.3 mg and the yield is 83%. Its XPRD pattern is substantially the same as FIG. 1.

Example 28

At room temperature, take 15.3 mg of the Known Crystal Form 2 of Dabrafenib and place it into a 20 mL-vial, add 1 mL of butanone, use the ultrasonic treatment for 5 mins to dissolve the sample completely (wherein the quantity of Dabrafenib is 1 time of its solubility in butanone at room temperature), in which add 10 mL of cyclohexane phase of the water-saturated cyclohexane solution dropwise to get white solid immediately, stir it for 8 days at 40° C., centrifugate, and dry it in a vacuum oven for 48 h at 40° C. to get Crystal Form VI of the present invention. The product is 7.3 mg and the yield is 46%. Its XPRD pattern is substantially the same as FIG. 1.

Example 29

At room temperature, take 20.1 mg of the amorphous form of Dabrafenib and place it into a 50 mL-vial, add 0.3 mL of tetrahydrofuran, use the ultrasonic treatment for 5 min to dissolve the sample completely (wherein the quantity of Dabrafenib is 1 time of its solubility in tetrahydrofuran at room temperature), in which add 30 mL of water dropwise to get white solid immediately, stir it for 1 week at room temperature, centrifugate, and dry it in a vacuum oven for 24 h at 40° C. to get Crystal Form VI of the present invention. The product is 15.2 mg and the yield is 76%. Its XPRD pattern is substantially the same as FIG. 1.

Example 30

At 60° C., take 3.5 mg of the Known Crystal Form 2 of Dabrafenib and place it into a 5 mL-vial, add 1 mL of nitromethane, use the ultrasonic treatment for 5 mins to dissolve the sample completely (wherein the quantity of Dabrafenib is 1 time of its solubility in nitromethane at room temperature), in which add 0.5 mL of methyl cyclohexane phase of the water-saturated methyl cyclohexane solution dropwisely to get white solid immediately, stir it for 14 days at 60° C., centrifugate, and dry it in a vacuum oven for 24 h at 40° C. to get Crystal Form VI of the present invention. The product is 2.1 mg and the yield is 60%. Its XPRD pattern is substantially the same as FIG. 1.

Example 31

At room temperature, take 6.5 mg of the Known Crystal Form 1 of Dabrafenib and place it into a 5 mL-vial, add 1 mL of acetonitrile, use the ultrasonic treatment for 5 mins to dissolve the sample completely (wherein the quantity of Dabrafenib is 1 time of its solubility in acetonitrile at room temperature), in which add 0.5 mL of water dropwise to get white solid immediately, stir it for 3 days at room temperature, centrifugate, and dry it in vacuum for 24 h at 40° C. to get Crystal Form VI of the present invention. The product is 6.2 mg and the yield is 95%. Its XPRD pattern is substantially the same as FIG. 1.

Example 32

Take 18.2 mg of the Known Crystal Form 2 of Dabrafenib and place it into a 5 mL-vial, add 0.8 mL of aqueous methanol solution (wherein the water volume content is 0.01%), heat to 50° C. in a water bath, stir until the sample is completely dissolved (wherein the quantity of Dabrafenib is 1 time of its solubility in the mentioned aqueous methanol solution at 50° C.), turn off the water bath to naturally cool to room temperature, then continue stirring for 3 days to get white solid, centrifugate, and dry it in vacuum for 24 h at room temperature to get Crystal Form VI of the present invention. The product is 11.6 mg and the yield is 64%. Its XPRD pattern is substantially the same as FIG. 1.

Example 33

Take 4.8 mg of the Known Crystal Form 2 of Dabrafenib and place it into a 5 mL-vial, add 3 mL water-saturated n-butanol solution and heat to 80° C. in a water bath, stir until the sample is completely dissolved (wherein the quantity of Dabrafenib is 1 time of its solubility in water-saturated n-butanol solution at 80° C.), close the water bath to naturally cool to room temperature, then continue stirring for 7 days to get white solid, centrifugate, and dry it in vacuum for 24 h at 40° C. to get Crystal Form VI of the present invention. The product is 1.6 mg and the yield is 33%. Its XPRD pattern is substantially the same as FIG. 1.

Example 34

Take 10.1 mg of the Known Crystal Form 2 of Dabrafenib and place it into a 5 mL-vial, add 0.1 mL of water-saturated ethyl acetate solution, heat to 60° C. in a water bath, stir until the sample is completely dissolved (wherein the quantity of Dabrafenib is 0.5 times of its solubility in water-saturated ethyl acetate solution at 60° C.), turn off the water bath to naturally cool to room temperature, then continue stirring for 7 days to get white solid, centrifugate, and dry it in vacuum for 24 h at 40° C. to get Crystal Form VI of the present invention. The product is 6.7 mg and the yield is 66%. Its XPRD pattern is substantially the same as FIG. 1.

Example 35

Take 8.6 mg of the Known Crystal Form 1 of Dabrafenib and place it into a 5 mL-vial, add 0.4 mL of water-saturated isopropyl acetate solution, heat to 40° C. in a water bath, stir until the sample is completely dissolved (wherein the quantity of Dabrafenib is 0.1 times of its solubility in water-saturated isopropyl acetate solution at 40° C.), stir for 14 days at 0° C. to get white solid, centrifugate, and dry it in vacuum for 24 h at 40° C. to get Crystal Form VI of the present invention. The product is 5.8 mg and the yield is 67%. Its XPRD pattern is substantially the same as FIG. 1.

Example 36

Take 8.1 mg of the Known Crystal Form 2 of Dabrafenib and place it into a 5 mL-vial, add 1 mL of water-saturated ethyl ether solution and heat to 50° C. in a water bath, stir until the sample is completely dissolved (wherein the quantity of Dabrafenib is 1 time of its solubility in water-saturated ethyl ether solution at 50° C.), turn off the water bath to naturally cool to room temperature, then continue stirring for 14 days to get white solid, centrifugate, and dry it in vacuum for 24 h at 40° C. to get Crystal Form VI of the present invention. The product is 3.0 mg and the yield is 37%. Its XPRD pattern is substantially the same as FIG. 1.

Example 37

Take 21.4 mg of the amorphous form of Dabrafenib and place it into a 5 mL-vial, add 5 mL of water-saturated methyl tert-butyl ether solution, heat to 50° C. in a water bath (wherein the quantity of Dabrafenib is 1 time of its solubility in water-saturated methyl tert-butyl ether solution at 50° C.), stir until the sample is completely dissolved, turn off the water bath to naturally cool to room temperature, then continue stirring for 14 days to get white solid, centrifugate, and dry it in vacuum for 24 h at room temperature to get Crystal Form VI of the present invention. The product is 10.3 mg and the yield is 48%. Its XPRD pattern is substantially the same as in FIG. 1.

Example 38

Take 11.4 mg of the Known Crystal Form 1 of Dabrafenib and place it into a 5 mL-vial, add 0.2 mL of aqueous acetone solution (wherein the water volume content is 0.1%) and heat to 50° C. in a water bath, stir until the sample is completely dissolved (wherein the quantity of Dabrafenib is 1 time of its solubility in the mentioned aqueous acetone solution at 50° C.), turn off the water bath to naturally cool to room temperature, then continue stirring for 3 days to get white solid, centrifugate, and dry it in vacuum for 24 h at 40° C. to get Crystal Form VI of the present invention. The product is 3.0 mg and the yield is 30%. Its XPRD pattern is substantially the same as FIG. 1.

Example 39

Take 11.2 mg of the Known Crystal Form 2 of Dabrafenib and place it into a 5 mL-vial, add 0.7 mL of water-saturated butanone solution and heat to 40° C. in a water bath, stir until the sample is completely dissolved (wherein the quantity of Dabrafenib is 0.1 times of its solubility in water-saturated acetone solution at 40° C.), stir for 14 days at 0° C. to get white solid, centrifugate, and dry it in vacuum for 24 h at 40° C. to get Crystal Form VI of the present invention. The product is 2.0 mg and the yield is 18%. Its XPRD pattern is substantially the same as FIG. 1.

Example 40

Take 7.3 mg of the Known Crystal Form 2 of Dabrafenib and place it into a 5 mL-vial, add 0.1 mL of aqueous tetrahydrofuran solution (wherein the water volume content is 50%) and heat to 50° C. in a water bath, stir until the sample is completely dissolved (wherein the quantity of Dabrafenib is 0.1 times of its solubility in the mentioned aqueous tetrahydrofuran solution at 50° C.), turn off the water bath to naturally cool to room temperature, then continue stirring for 3 days to get white solid, centrifugate, and dry it in a vacuum oven for 24 h at 40° C. to get Crystal Form VI of the present invention. The product is 1.2 mg and the yield is 16%. Its XPRD pattern is substantially the same as FIG. 1.

Example 41

Take 8.1 mg of the Known Crystal Form 1 of Dabrafenib and place it into a 5 mL-vial, add 1 mL of water-saturated nitromethane solution and heat to 40° C. in a water bath, stir until the sample is completely dissolved (wherein the quantity of Dabrafenib is 0.5 times of its solubility in water-saturated nitromethane solution at 80° C.), turn off the water bath to naturally cool to room temperature, then continue stirring for 7 days to get white solid, centrifugate, and dry it in vacuum for 24 h at 40° C. to get Crystal Form VI of the present invention. The product is 5.0 mg and the yield is 62%. Its XPRD pattern is substantially the same as FIG. 1.

Example 42

Take 12.3 mg of the amorphous form of Dabrafenib and place it into a 5 mL-vial, add 0.8 mL of aqueous acetonitrile solution (wherein the water volume content is 50%) and heat to 80° C. in a water bath, stir until the sample is completely dissolved (wherein the quantity of Dabrafenib is 0.5 times of its solubility in the mentioned aqueous acetonitrile solution at 80° C.), turn off the water bath to naturally cool to room temperature, then continue stirring for 1 week to get white solid, centrifugate, and dry it in vacuum for 16 h at 40° C. to get Crystal Form VI of the present invention. The product is 4.2 mg and the yield is 34%. Its XPRD pattern is substantially the same as FIG. 1.

Example 43

At room temperature, take 5.0 mg of the Known Crystal Form 2 of Dabrafenib and place it into a 20 mL-vial, add 1.7 mL of isopropyl acetate, use the ultrasonic treatment until the solution becomes clear, then filter it with 0.45 μm membrane, place the uncovered vial filled with the filtrate in a sealed 100 mL space filled with 15 mL of isopropyl ether—for 3 weeks, centrifugate until after isopropyl ether diffused into the isopropyl acetate solution and a great amount of solids emerge, dry it in a vacuum oven for 24 h at 40° C. to get Crystal Form VII of the present invention. The product is 4.0 mg and the yield is 80%.

Figure 8:
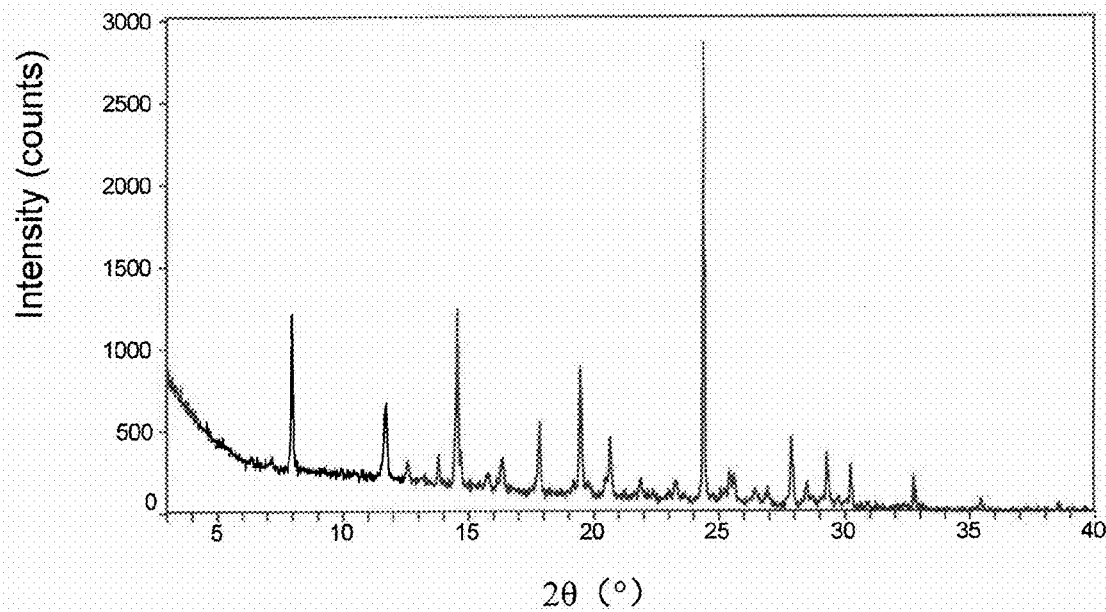
FIG. 8 is the X-ray powder diffraction pattern of Crystal Form VII of the present invention.

The XPRD pattern is as shown in FIG. 8.

Figure 9:
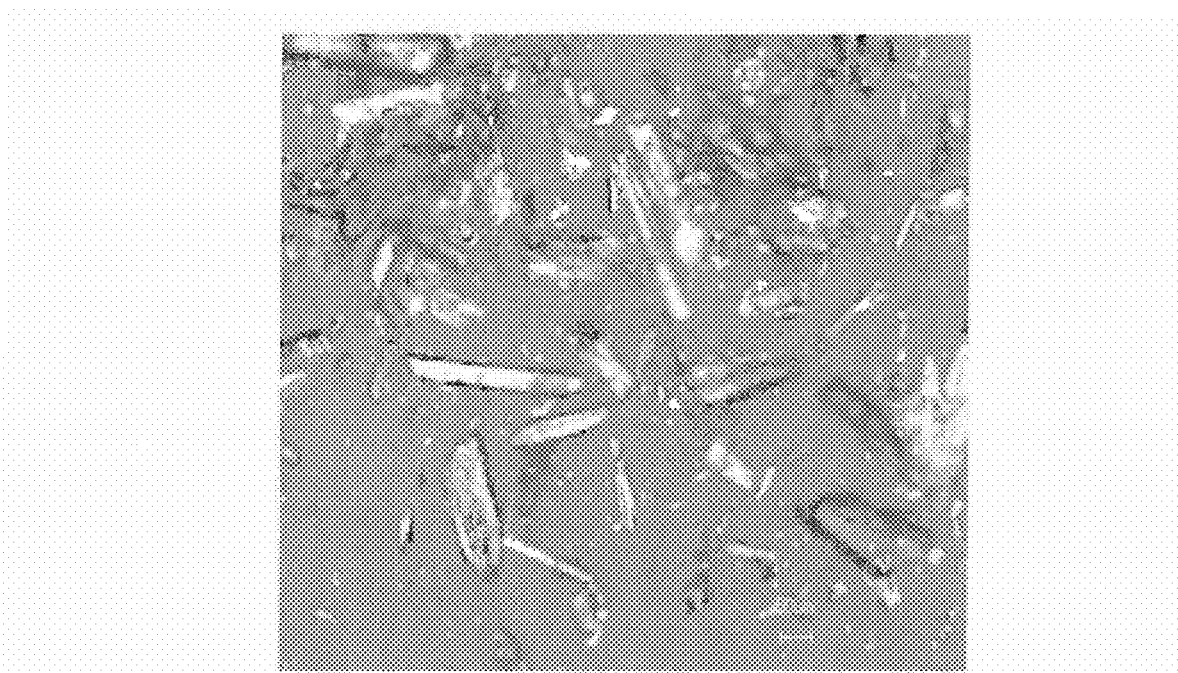
FIG. 9 is the PLM plot of Crystal Form VII of the present invention.

The PLM plot is as shown in FIG. 9. It shows rod-shaped crystals.

PSD shows: D10, D50 and D90 are 91 μm, 207 μm and 378 μm, respectively. And the particle size is larger than that of the Known Crystal Form 1 and the Known Crystal Form 2.

Figure 10:
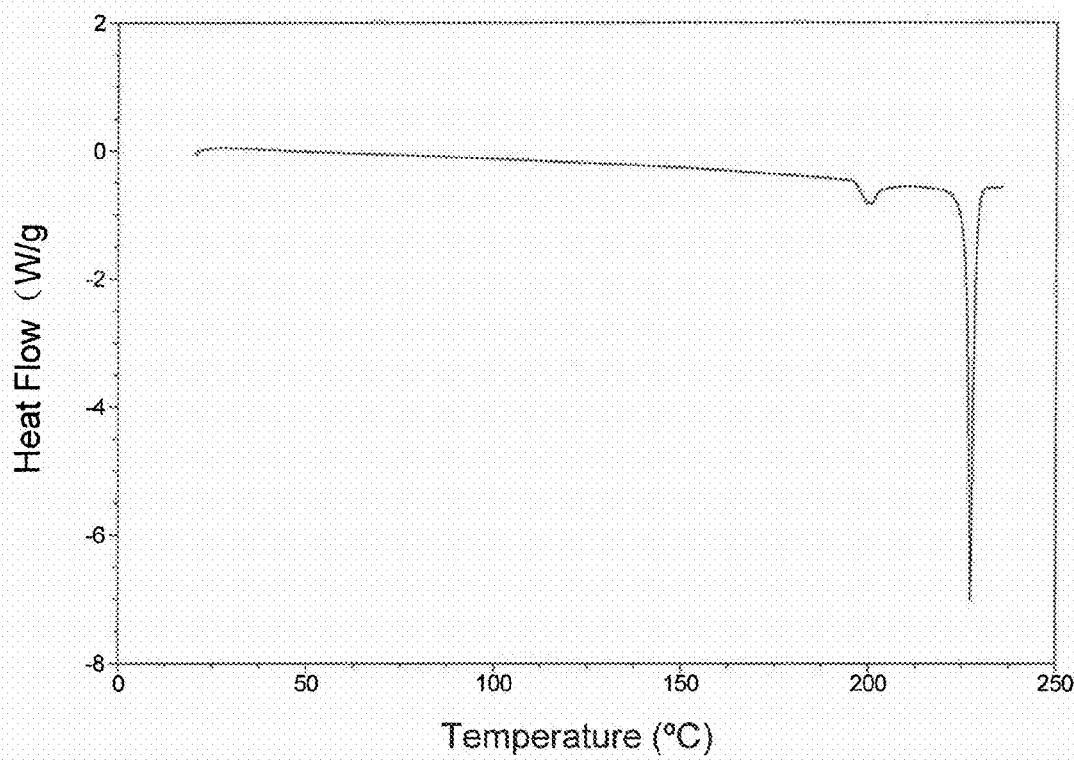
FIG. 10 is the DSC thermogram of Crystal Form VII of the present invention.

The DSC thermogram is as shown in FIG. 10. It shows: Crystal Form VII has a small endothermic peak at 192~211° C. and the melting point thereafter is 226° C.

Figure 11:
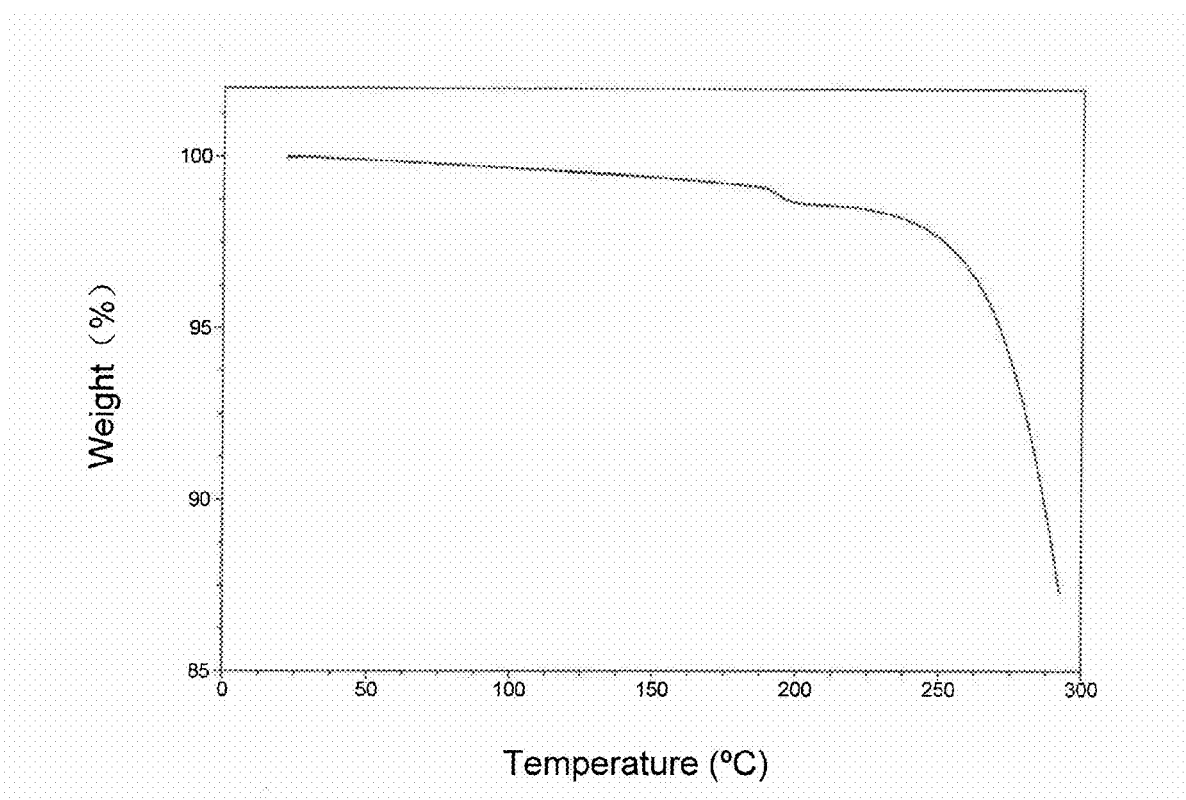
FIG. 11 is the TGA thermogram of Crystal Form VII of the present invention.

The TGA thermogram is as shown in FIG. 11. It shows: Crystal Form VII has almost no weight loss prior to 175° C., about 0.6% weight loss between 175° C.~212° C. and the decomposition temperature is 270° C.

Figure 12:
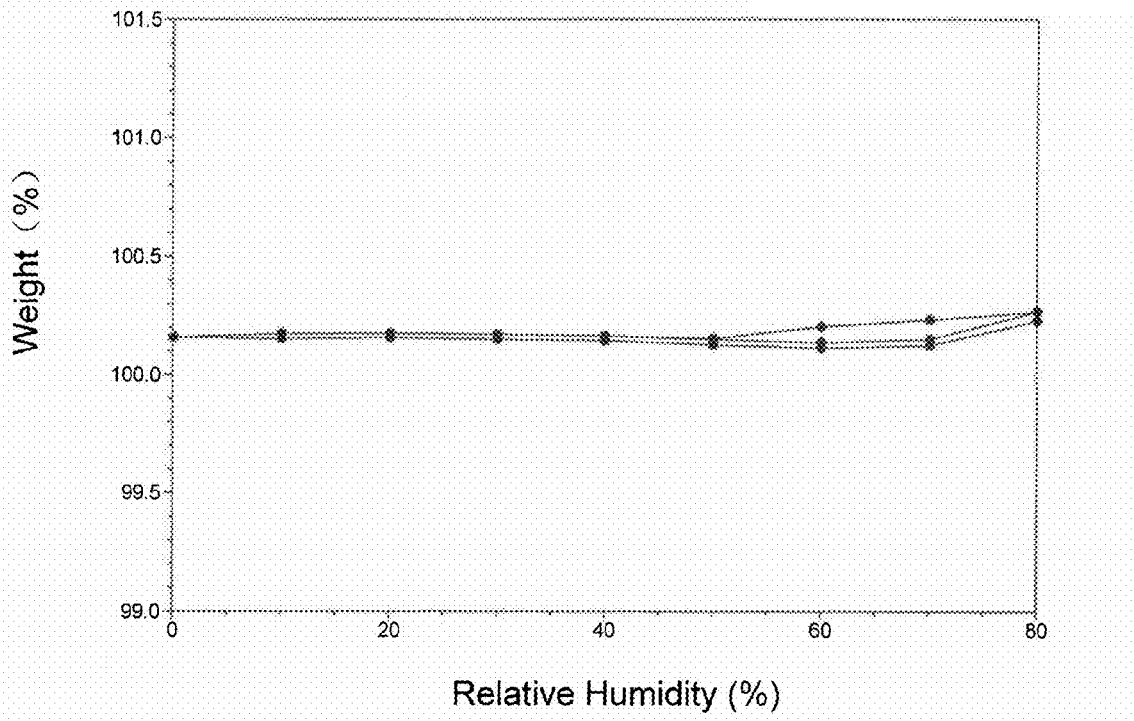
FIG. 12 is the dynamic vapor sorption isotherm of Crystal Form VII of the present invention.

The dynamic vapor sorption isotherm is as shown in FIG. 12. It shows: the weight change is 0.1% between 20% RH~80% RH.

The above test results show that Crystal Form VII has good morphology, is very stable at high temperature, and has low hygroscopicity.

Example 44

At room temperature, take 5.0 mg of the Known Crystal Form 1 of Dabrafenib and place it into a 20 mL-vial, add 1.0 mL of isopropyl acetate, use the ultrasonic treatment until the solution becomes clear, then filter it with 0.45 μm organic filter membrane, place the vial filled with the filtrate in a sealed 100 mL-space filled with 15 mL of mineral ether—for 1 week, centrifugate until after mineral ether diffused into the isopropyl acetate solution and a great amount of solids emerge, and dry it in vacuum for 24 h at 40° C. to get Crystal Form VII of the present invention. The product is 2.7 mg and the yield is 54%. Its XPRD pattern is substantially the same as FIG. 8.

Example 45

Figure 13:
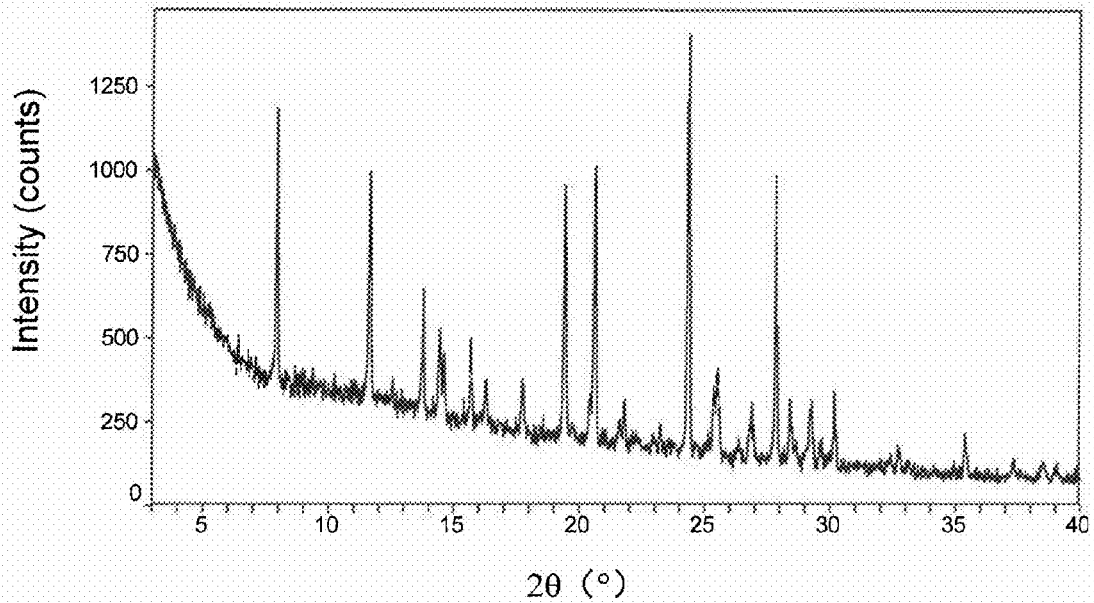
FIG. 13 is another X-ray powder diffraction pattern of Crystal Form VII of the present invention.

Take 3.2 mg of the Known Crystal Form 2 of Dabrafenib and place it into a 5 mL-vial, add 0.2 mL of ethyl acetate, use the ultrasonic treatment until the solution becomes clear, then filter it with 0.45 min organic filter membrane, place the vial filled with the filtrate (wherein the quantity of Dabrafenib is 0.5 times of its solubility in ethyl acetate at room temperature) at room temperature to volatilize and crystallize for 7 days, centrifuge the solid obtained, dry it in vacuum for 24 h at 40° C. to get Crystal Form VII of the present invention. The product is 2.0 mg and the yield is 62%. The XPRD pattern is as shown in FIG. 13 and is substantially the same as FIG. 8.

Example 46

Figure 14:
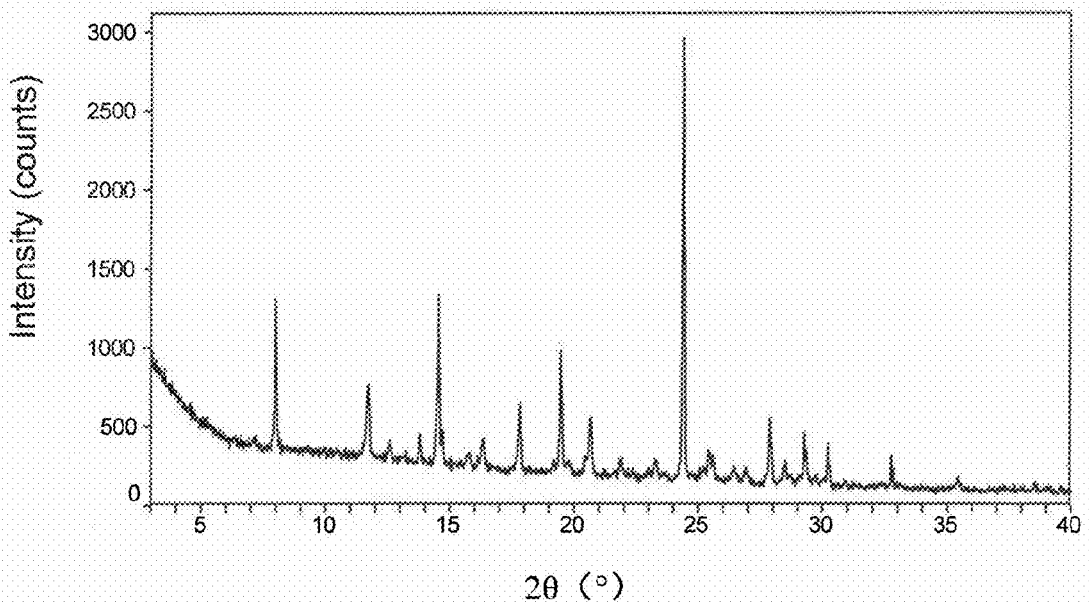
FIG. 14 is another X-ray powder diffraction pattern of Crystal Form VII of the present invention.

Take 4.3 mg of Crystal Form VI of Dabrafenib, heat it up to 125° C. at 10° C./min to remove the crystalline water, then cool naturally to room temperature, and dry the obtained crystals in a vacuum oven for 24 h at 40° C. to get Crystal Form VII of the present invention. The product is 4.0 mg and the yield is 93%. The XPRD pattern is as shown in FIG. 14 and is substantially the same as FIG. 8.

Example 47

Take 10.1 mg of the oily form (the amorphous form) of Dabrafenib and place it into a 5 mL-vial, add 0.2 mL of isopropanol to form a suspension (wherein the quantity of the amorphous form is 10 times of its solubility in isopropanol at room temperature), stir to crystallize for 2 h, immediately centrifugate after the white solids emerge, dry it in vacuum for 24 h at 40° C. to get Crystal Form VII of the present invention. The product is 9.0 mg and the yield is 89%. Its XPRD pattern is substantially the same as FIG. 8.

Example 48

Take 1.0 mg of the oily form (the amorphous form) of Dabrafenib and place it into a 5 mL-vial, add 5.0 mL of n-butanol to form a suspension (wherein the quantity of the amorphous form is 2 times of its solubility in butanol at room temperature), stir to crystallize for 0.2 h, immediately centrifugate after the white solids emerge, dry it in a vacuum oven for 24 h at 40° C. to get Crystal Form VII of the present invention. The product is 0.7 mg and the yield is 70%. Its XPRD pattern is substantially the same as FIG. 8.

Example 49

Take 7.9 mg of the Known Crystal Form 2 of Dabrafenib and place it into a 5 mL-vial, add 1.0 mL of ethanol, use the ultrasonic treatment until the solution becomes clear, then filter it with 0.45 μm organic filter membrane, add the filtrate (wherein the quantity of Dabrafenib is 0.5 times of its solubility in ethanol at room temperature) to a 30 ml-vial filled with 25 mL of n-heptane, stir it at room temperature for 1min until the white solid precipitated, immediately centrifugate it, dry it in vacuum for 24 h at 40° C. to get Crystal Form VII of the present invention. The product is 6.5 mg and the yield is 82%. Its XPRD pattern is substantially the same as FIG. 8.

Example 50

Take 8.4 mg of the Known Crystal Form 2 of Dabrafenib and place it into a 5 mL-vial, add 2 mL of ethyl ether, use the ultrasonic treatment until the solution becomes clear, then filter it with 0.45 μm organic filter membrane, add the filtrate (wherein the quantity of Dabrafenib is 1 times of its solubility in ethyl ether at room temperature) to a 20 ml-vial filled with 10 mL of methyl cyclohexane, stir it at room temperature for 30 min until the white solid precipitated, immediately centrifugate it, dry it in vacuum for 24 h at 40° C. to get Crystal Form VII of the present invention. The product is 6.5 mg and the yield is 77%. Its XPRD pattern is substantially the same as FIG. 8.

Example 51

Take 7.9 mg of the amorphous form of Dabrafenib and place it into a 5 mL-vial, add 2 mL of 1,4-dioxane, use the ultrasonic treatment until the solution becomes clear, then filter it with 0.45 μm organic filter membrane, add the filtrate (wherein the quantity of Dabrafenib is 0.1 times of its solubility in 1,4-dioxane at room temperature) to a 25 ml-vial filled with 20 mL of water, stir it at room temperature for 60 min until the white solid precipitated, immediately centrifugate it, dry it in a vacuum oven for 24 h at 40° C. to get Crystal Form VII of the present invention. The product is 2.4 mg and the yield is 30%. Its XPRD pattern is substantially the same as FIG. 8.

Example 52

Take 4.9 mg of the Known Crystal Form 1 of Dabrafenib and place it into a 5 mL vial, add 0.5 mL of isopropanol, use the ultrasonic treatment until the solution becomes clear, then filter it with 0.45 μm organic filter membrane, add the filtrate (wherein the quantity of Dabrafenib is 1 time of its solubility in isopropanol at room temperature) to a 20 ml-vial filled with 5 mL of cyclohexane, stir it at room temperature for 30 min until the white solid precipitated, immediately centrifugate it, dry it in vacuum for 24 h at 40° C. to get Crystal Form VII of the present invention. The product is 1.8 mg and the yield is 37%. Its XPRD pattern is substantially the same as FIG. 8.

Example 53

Figure 15:
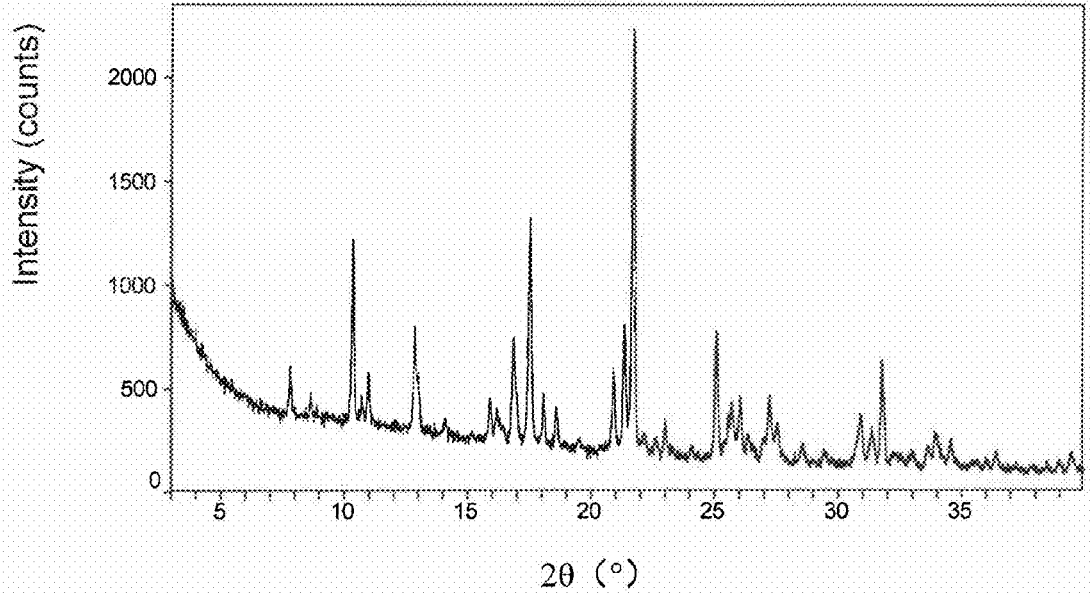
FIG. 15 is the X-ray powder diffraction pattern of Crystal Form III of the present invention.

Take 7.8 mg of the Known Crystal Form 2 of Dabrafenib and place it into a 5 mL-vial, add 1 mL of sec-butanol, take the ultrasonic treatment to get a suspension, stir it at room temperature for 7 days, centrifugate, without drying, get Crystal Form III of the present invention. The product is 7.0 mg and the yield is 90%. Its XPRD pattern is as shown in FIG. 15.

Example 54

Figure 16:
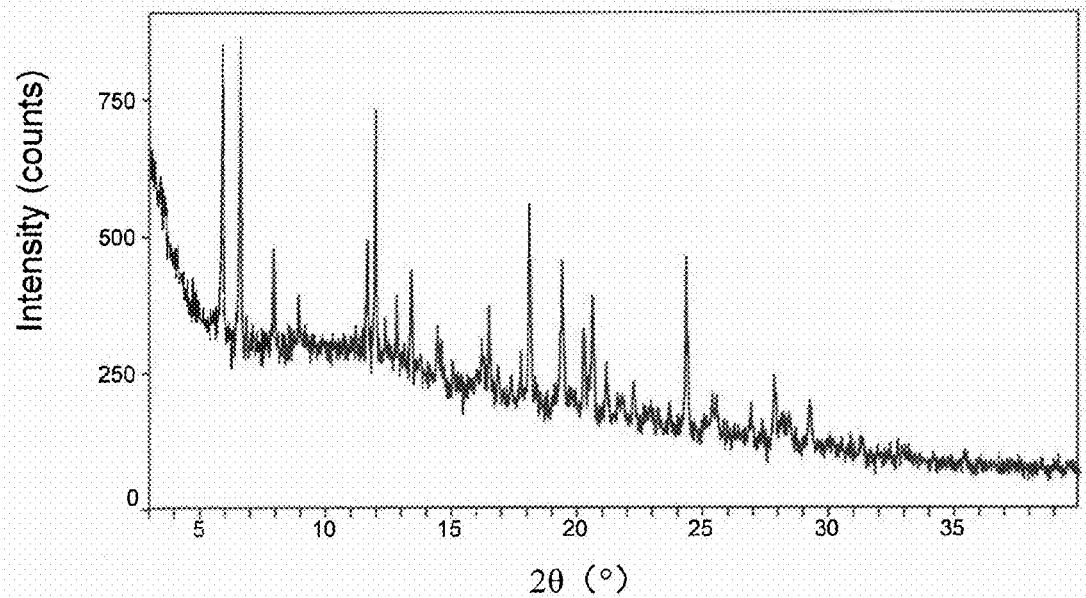
FIG. 16 is the X-ray powder diffraction pattern of Crystal Form IV of the present invention.

Take 20.0 mg of the Known Crystal Form 2 of Dabrafenib and place it into a 5 mL-vial, add 1 mL methyl tert-butyl ether, use the ultrasonic treatment until the solution becomes clear, then filter it with 0.45 μm organic filter membrane, place the vial filled with the filtrate to evaporate at room temperature for 1 week, centrifugate the precipitated crystal, without drying, get Crystal Form IV of the present invention. The product is 17.0 mg and the yield is 85%. Its XPRD pattern is as shown in FIG. 16.

Example 55

Figure 17:
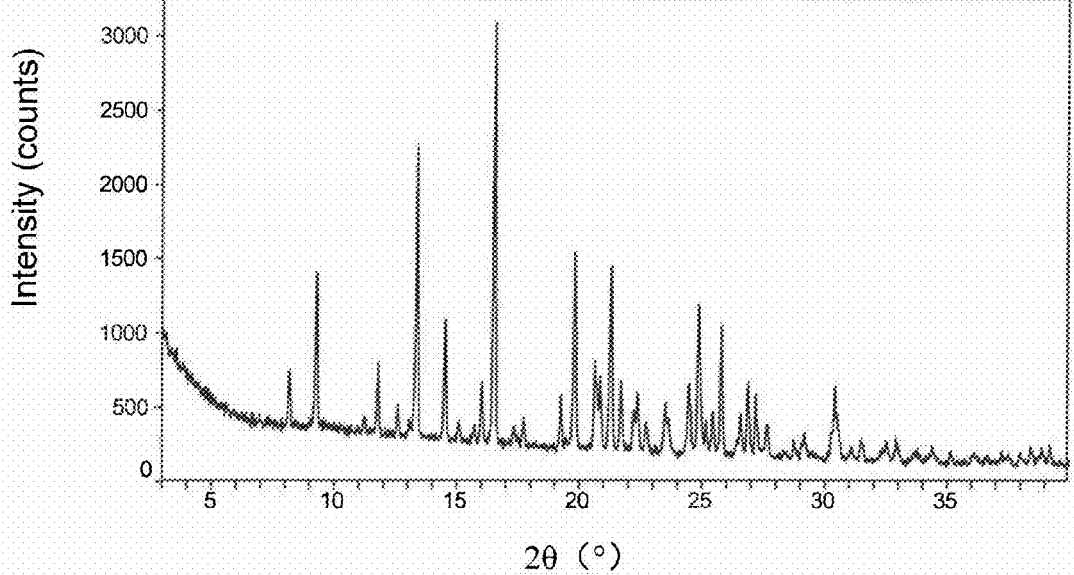
FIG. 17 is the X-ray powder diffraction pattern of Crystal Form V of the present invention.

Take 10.6 mg of the Known Crystal Form 2 of Dabrafenib and place it into a 5 mL-vial, add 1 mL dichloromethane, use the ultrasonic treatment to get a suspension, stir it at room temperature for 7 days, centrifugate, without drying, get Crystal Form V of the present invention. The product is 7 mg and the yield is 66%. Its XPRD pattern is as shown in FIG. 17.

Example 56

Figure 18:
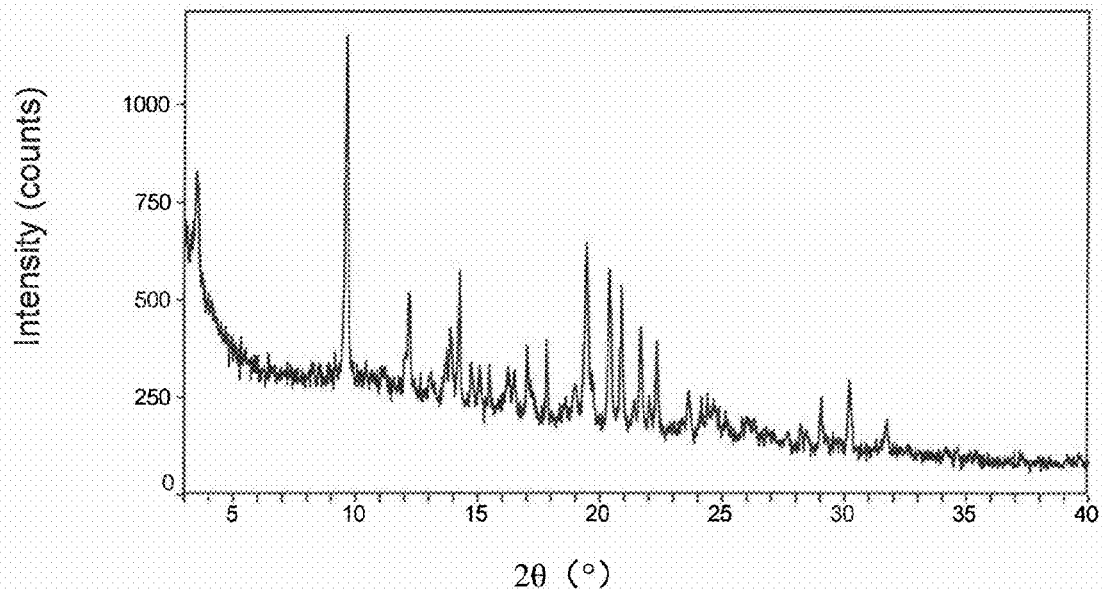
FIG. 18 is the X-ray powder diffraction pattern of Crystal Form VIII of the present invention.

Take 15.0 mg of the Known Crystal Form 2 of Dabrafenib and place it into a 20 mL-vial, add 4 mL of ethyl acetate, use the ultrasonic treatment until the solution becomes clear, then filter it with 0.45 μm organic filter membrane, place the vial filled with the filtrate in a sealed 100 mL space filled with 15 mL of isopropyl ether—for 3 weeks, centrifugate until after isopropyl ether diffused into the ethyl acetate solution and a great amount of solids emerge, then keep it for 2 h at room temperature to get Crystal Form VIII of the present invention. The product is 10.0 mg and the yield is 67%. Its XPRD pattern is as shown in FIG. 18.

Example 57

Figure 19:
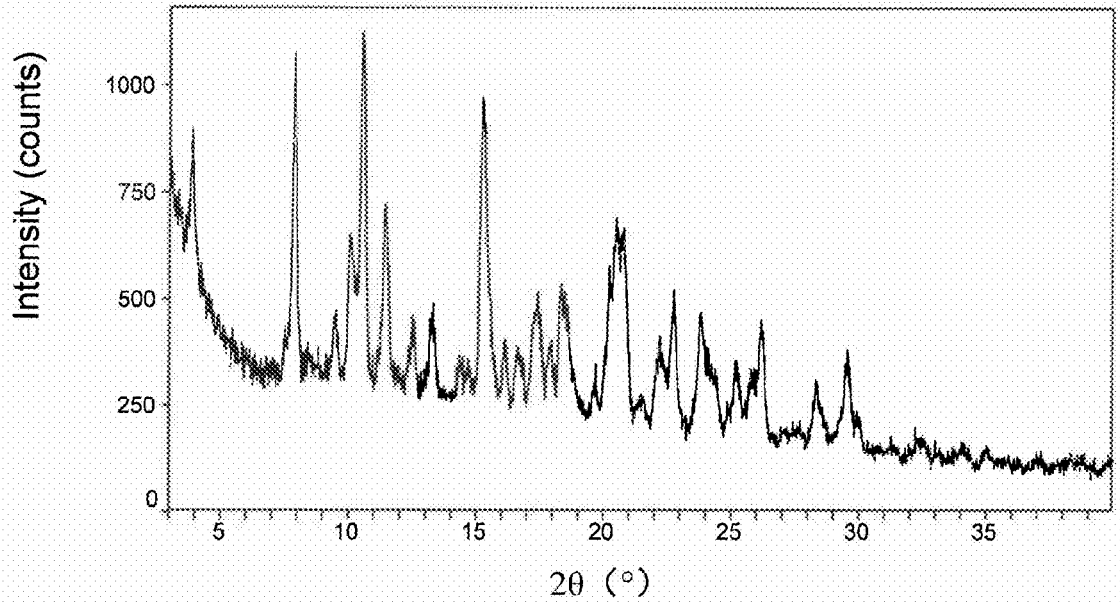
FIG. 19 is the X-ray powder diffraction pattern of Crystal Form Ie of the present invention.

Take 10.0 mg of the Known Crystal Form 2 of Dabrafenib and place it into a 5 mL-vial, add 3 mL of toluene, raise the temperature to 60° C. until the solution becomes clear, filter it without cooling, then directly place the container filled with the filtrate into an environment at 0° C., immediately the solids precipitate, stir it for 0.2 h and then centrifugate, without drying, get Crystal Form Ie of the present invention. The product is 5.4 mg and the yield is 54%. Its XPRD pattern is as shown in FIG. 19.

Example 58

Take 10.9 mg of the Known Crystal Form 2 of Dabrafenib and place it into a 5 mL-vial, add 2 mL of ethanol, use the ultrasonic treatment until the solution becomes clear, then filter it with 0.45 μm organic filter membrane, rapidly rotary evaporate to dry to get an oil (an amorphous form). At room temperature, add 1 mL of toluene to form a suspension, stir it for 2 h, immediately the solid is precipitated, centrifugate, without drying, get Crystal Form Ie of the present invention. The product is 5.8 mg and the yield is 53%. Its XPRD pattern is as shown in FIG. 19.

Example 59

Figure 20:
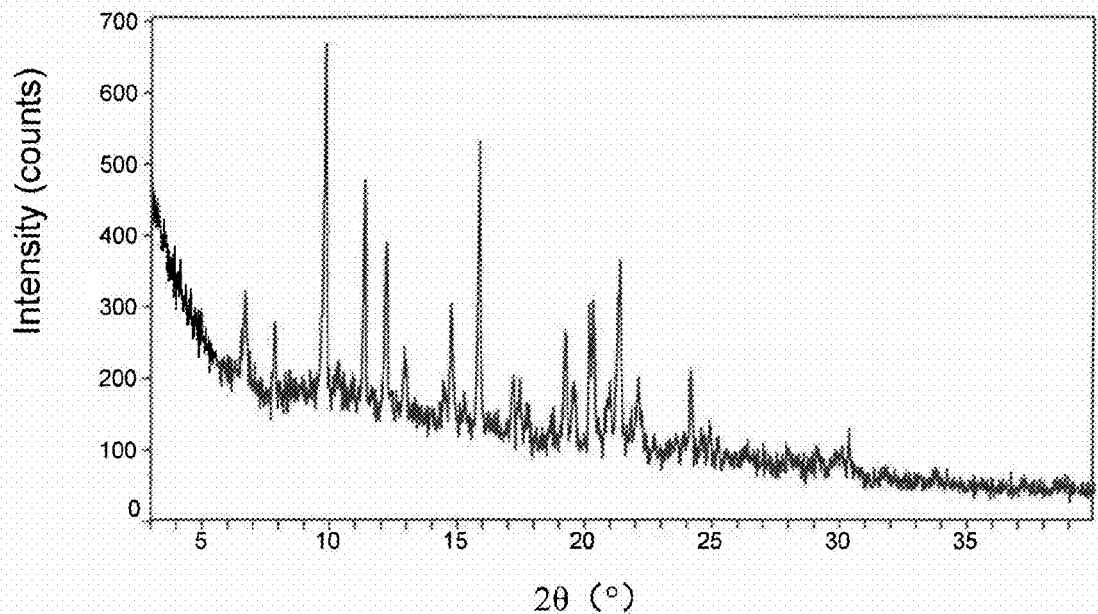
FIG. 20 is the X-ray powder diffraction pattern of Crystal Form VIIb of the present invention.

Take 10.4 mg of the Known Crystal Form 2 of Dabrafenib and place it into a 5 mL-vial, add 1 mL of butanone, use the ultrasonic treatment until the solution becomes clear, then filter it with 0.45 μm organic filter membrane, add 1 mL of methyl cyclohexane to the filtrate, immediately the solid is precipitated, centrifugate, directly take the wet sample (still containing some solvent) to get Crystal Form VIIb of the present invention. The product is 10.3 mg and the yield is 99%. Its XPRD pattern is as shown in FIG. 20.

Example 60

Figure 21:
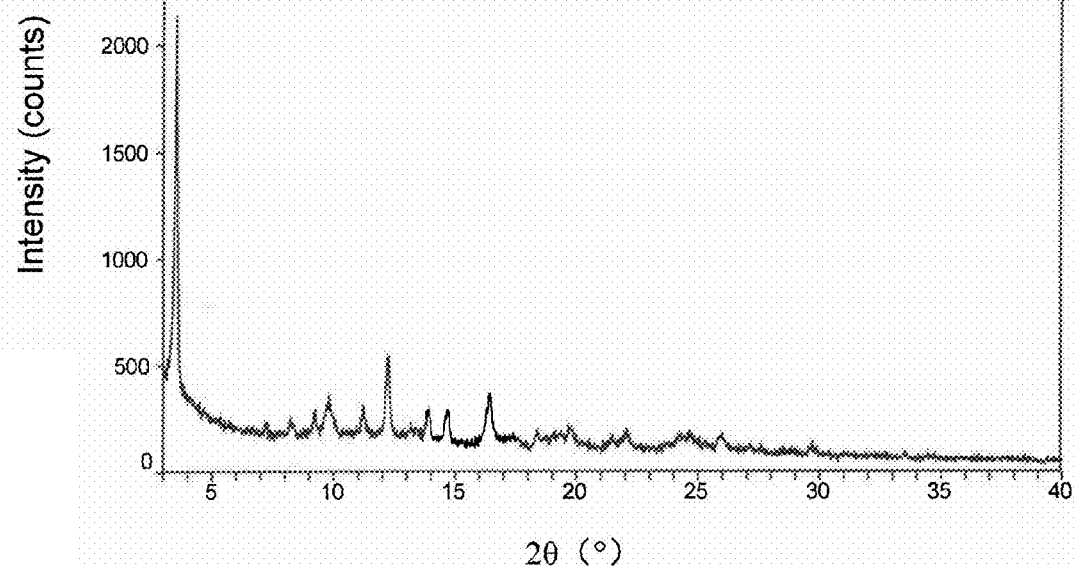
FIG. 21 is the X-ray powder diffraction pattern of Crystal Form VIIIa of the present invention.

Take 15.0 mg of the Known Crystal Form 2 of Dabrafenib and place it into a 20 mL-vial, add 2 mL of ethyl acetate, use the ultrasonic treatment until the solution becomes clear, then filter it with 0.45 μm organic filter membrane, place the vial filled with the filtrate in a sealed 100 mL space filled with 15 mL of isopropyl ether—at 30° C. for 7 days, centrifugate until after isopropyl ether diffused into the ethyl acetate solution and a great amount of solids emerge, directly take the wet sample (still containing some solvent) without drying to get Crystal Form VIIIa of the present invention. The product is 15.0 mg and the yield is 100%. Its XPRD pattern is as shown in FIG. 21.

Experimental Example 1

Take Crystal Form VI of the present invention prepared by Example 1, Crystal Form VII of the present invention prepared by Example 43, the Known Crystal Form 1 prepared by Preparation Example 1 and the Known Crystal Form 2 prepared by Preparation Example 2, and compare them in stability, hygroscopicity and morphology. As the Known Crystal Form 3 is extremely unstable and converts to the Known Crystal Form 1 when placed at room temperature, it is not used for comparison.

The stability is compared by the storage stability and the competition test.

The storage stability test is: storing the sample under constant conditions (i.e. constant humidity or constant temperature) for a certain time, and then comparing the XRPDs before and after storing.

The competition test is: take equal amount of the samples, and respectively place them in isopropanol or in a mixture of water (pure water) and ethanol (wherein the volume percentage of ethanol is 0%, 20%, 50%, 80% and 100%, respectively) to form a suspension, stir it overnight at room temperature, then compare their XRPDs.

The hygroscopicity is obtained by DVS testing of the weight changes between 20%-80% RH.

The morphology comparison is obtained by PLM testing of particle shape and PSD testing of particle size.

The results are shown in the following Table 1.

TABLE 1

Property Comparison Results of Different Crystal Forms

| Properties | Crystal form | | | |
|---|---|---|---|---|
| | the Known Crystal Form 2 | the Known Crystal Form 1 | Crystal Form VI of the present invention | Crystal Form VII of the present invention |
| Hygroscopicity (weight changes between 20%-80% RH) | 0.03% (FIG. 24) | 1.9% (FIG. 27) | 0.49% (FIG. 5) | 0.09% (FIG. 12) |
| Morphology | small block particles (FIG. 23), D10, D50 and D90 are 16 μm 36 μm and 74 μm, respectively. | small block particles (FIG. 26), D10, D50 and D90 are 50 μm 104 μm and 151 μm, respectively. | Fine particles (FIG. 2), D10, D50 and D90 are 7 μm, 18 μm and 40 μm, respectively. | Rod shape (FIG. 9), D10, D50 and D90 are 91 μm, 207 μm and 378 μm, respectively. |

TABLE 1-continued

Property Comparison Results of Different Crystal Forms

| | | Crystal form | | | |
|---|---|---|---|---|---|
| Properties | | the Known Crystal Form 2 | the Known Crystal Form 1 | Crystal Form VI of the present invention | Crystal Form VII of the present invention |
| Stability | Storage stability | Stable after storing for 3 months in the desiccator at room temperature, at room temperature-97% RH, at room temperature-75% RH, at room temperature-44% RH or in the oven of 40° C. | | | |
| | Competition test | In pure water, comparison of stability: Crystal Form VI of the present invention >The Known Crystal Form 1 >Crystal Form VII of the present invention >The Known Crystal Form 2. In aqueous ethanol solution (wherein the volume percentage of ethanol is 20%, 50% and 80% respectively), comparison of stability: Crystal Form VI of the present invention >the other three crystal forms. In isopropanol or ethanol, comparison of stability: The Known Crystal Form 1 >The other three crystal forms. | | | |

According to the results observed in the experiments, Crystal Form VI of the present invention is the most stable crystal form in the aqueous system. The Known Crystal Form 1, the Known Crystal Form 2 and Crystal Form VII of the present invention, if stirred in water or aqueous ethanol solution at room temperature or high temperature, all convert to Crystal Form VI of the present invention. In contrast, Crystal Form VI of the present invention keeps unchanged under the same conditions; Crystal Form VI of the present invention has low hygroscopicity; and Crystal Form VI of the present invention has good storage stability, it is stable when stored for a long time in the desiccator at room temperature, at room temperature-97% RH, at room temperature-75% RH, at room temperature-44% RH or in the oven of 40° C.

During the experiments, it is also found that Crystal Form VII of the present invention is of rod-shaped particles in large size and has good flowability; Crystal Form VII of the present invention has low hygroscopicity; and Crystal Form VII of the present invention has good storage stability, it is stable when stored for a long time in the desiccator at room temperature, at room temperature-97% RH, at room temperature-75% RH, at room temperature-44% RH or in the oven of 40° C.

Experimental Example 2

The Known Crystal Form 1, the Known Crystal Form 2 and Crystal Form VI of the present invention are examined for their stability during the formulation preparation of the wet granulation process.

The preparation process of the tablet is a parallel experiment. The formulation of tablets is as shown in Table 2 below.

TABLE 2

Tablet formulation

| Ingredient | Content (mg/tablet) |
|---|---|
| Pharmaceutical active ingredient (API) | 100 |
| Lactose (monohydrate) | 280 |
| Microcrystalline cellulose | 112 |
| Polyethylene glycol 6000 | 8 |

The steps to prepare the tablet are as follows:

(1) Blend API (selected from the Known Crystal Form 1, the Known Crystal Form 2 or Crystal Form VI of the present invention), lactose (monohydrate) and microcrystalline cellulose uniformly.

(2) Make the above mixture into soft materials by using an appropriate amount of 50% aqueous ethanol solution, screen to produce the wet granules and then dry the wet granules.

(3) Granulate the dried sample, blend with polyethylene glycol 6000 uniformly and then compress into tablets.

Respectively, take XRPD tests on the following samples obtained in the formulation preparing process of the Known Crystal Form 1, the Known Crystal Form 2 and Crystal Form VI of the present invention: (Sample 1) the sample obtained by physically blending API, lactose, microcrystalline cellulose with polyethylene glycol 6000 according to the preparation formula; (Sample 2) the sample obtained by granulating with API, lactose, microcrystalline cellulose and polyethylene glycol 6000 according to the "wet granulation" process (excluding the sample obtained after the Step (3)); (Sample 3) excluding API, the sample obtained by physically blending lactose, microcrystalline cellulose with polyethylene glycol 6000 according to the preparation formula. The XRPD patterns of Samples 1-3 are shown in FIGS. 28-30.

Figure 29:
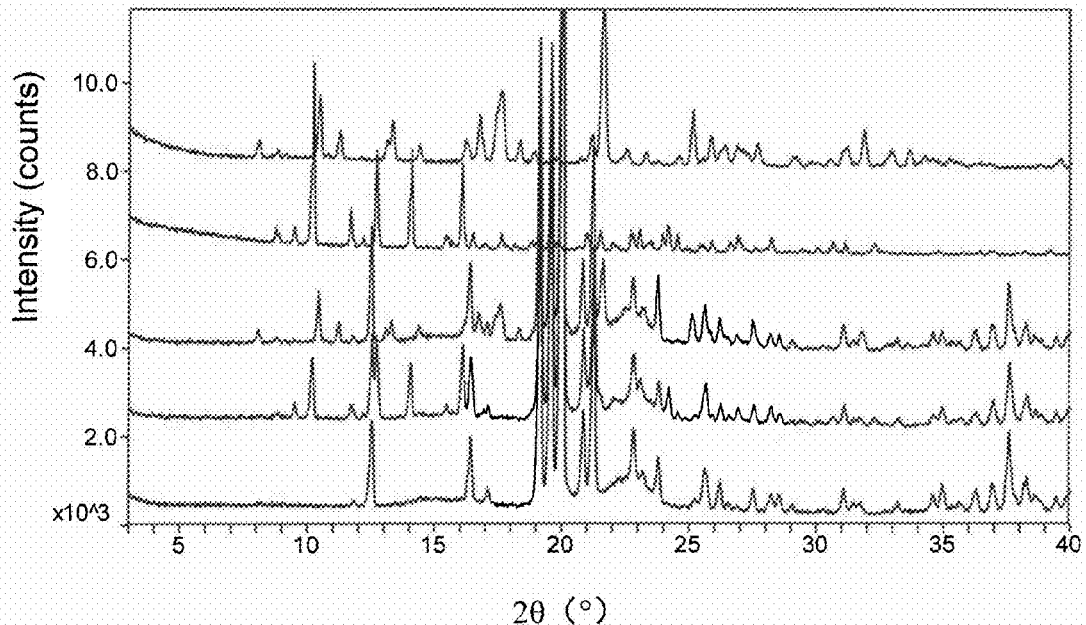
FIG. 29 is the X-ray powder diffraction comparison pattern of the Known Crystal Form 1 at various stages in Experimental Example 2 (in the figure, the samples from top to bottom are: Crystal Form VI, the Known Crystal Form 1; the sample obtained by the wet granulation process with the Known Crystal Form 1 as API; the sample obtained by physically blending the Known Crystal Form 1 and the excipients according to the formula quantity of the preparation; and the sample obtained by physically blending the excipients according to the formula quantity of the preparation).
Figure 30:
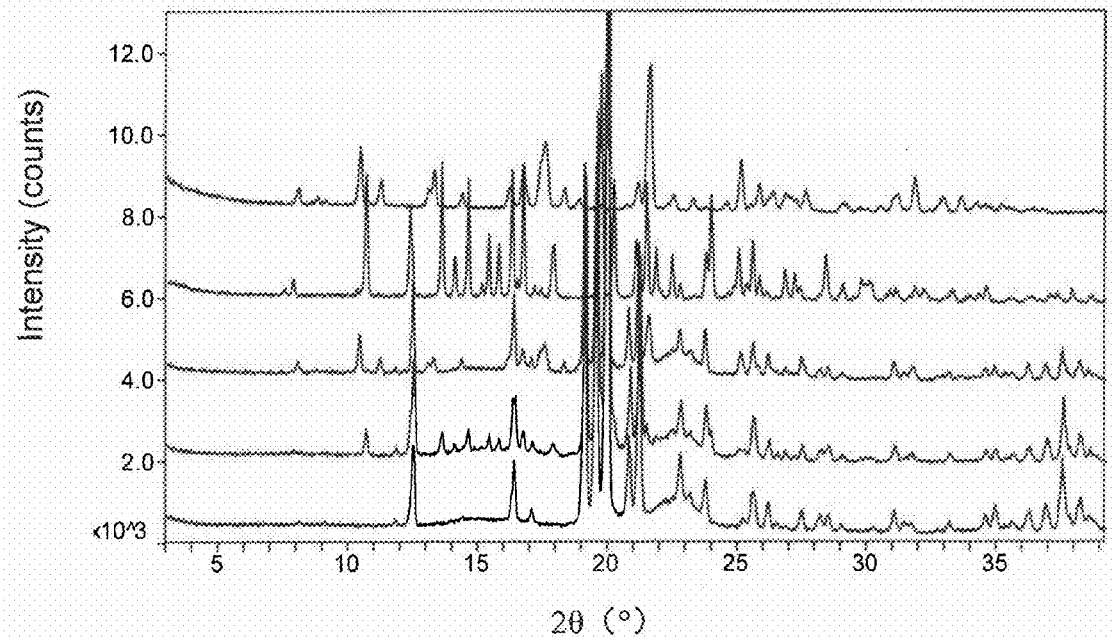
FIG. 30 is the X-ray powder diffraction comparison pattern of the Known Crystal Form 2 at various stages in Experimental Example 2 (in the figure, the samples from top to bottom are followed by: Crystal Form VI; the Known Crystal Form 2; the sample obtained by the wet granulation process with the Known Crystal Form 2 as API; the sample obtained by physically blending the Known Crystal Form 2 and the excipients according to the formula quantity of the preparation; and the sample obtained by physically blending the excipients according to the formula quantity of the preparation).

According to FIG. 29 and FIG. 30, it is shown that in respect of the Known Crystal Form 1 or the Known Crystal Form 2 as API, the comparison of XRPD patterns of its Sample 1 and its Sample 3 shows that the crystal form of API keeps unchanged after API is physically blended with the excipients; however, the comparison of XRPD patterns of its Sample 2 and its Sample 1 shows that API in Sample 2 has partially or totally converted to Crystal Form VI of the present invention, which indicates that the Known Crystal Form 1 and the Known Crystal Form 2 are unstable in the wet granulation process and convert to the more stable Crystal Form VI of the present invention.

Figure 28:
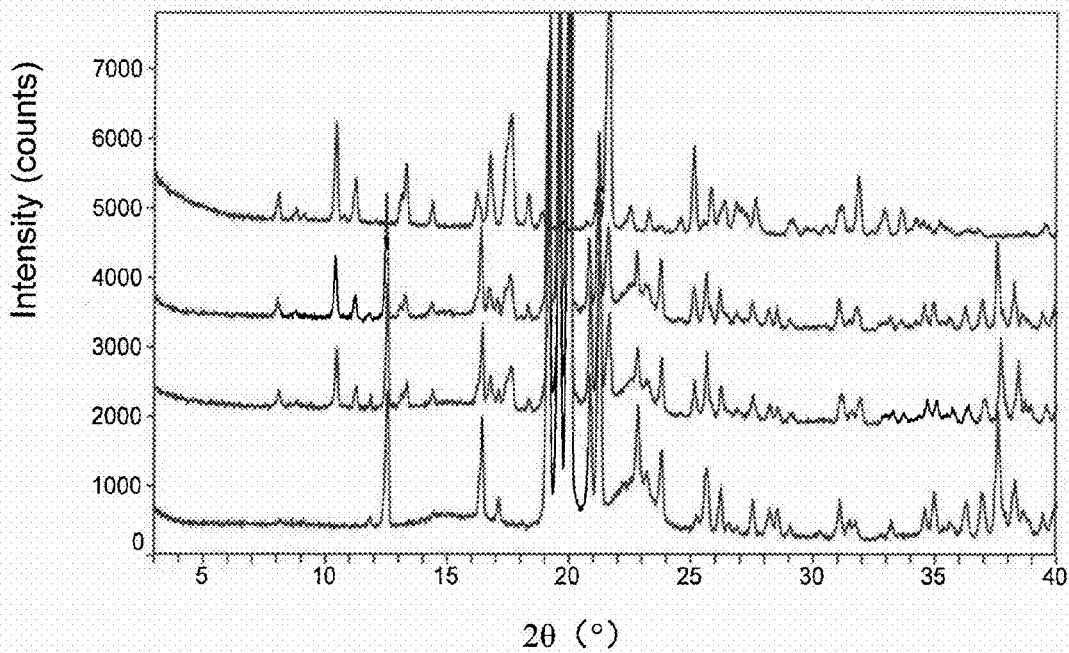
FIG. 28 is the X-ray powder diffraction comparison pattern of Crystal Form VI at various stages in Experimental Example 2 of the present invention (in the figure, the samples from top to bottom are: Crystal Form VI; the sample obtained by physically blending Crystal Form VI and the excipients according to the formula quantity of the preparation; the sample obtained by the wet granulation process with Crystal Form VI as API; and the sample obtained by physically blending the excipients according to the formula quantity of the preparation).

According to FIG. 28, it is shown that in respect of Crystal Form VI of the present invention as API, the comparison of XRPD patterns of its Sample 1 and its Sample 3 shows that the crystal form of API keeps unchanged after API is physically blended with the excipients; the consistency of XRPD patterns of its Sample 1 and its Sample 2 shows that Crystal Form VI of the present invention is stable in the wet granulation process.

It is also discovered that Crystal Form VI of the present invention is stable after tableting.

Therefore, Crystal Form VI of the present invention is more stable than the Known Crystal Form 1 and the Known Crystal Form 2 in the wet granulation process of tableting, and it is also stable after tableting. It has good preparation processing adaptability and thus it is the advantageous crystal form.

It is also discovered that the tablet containing Crystal Form VI prepared by the wet granulation process is still stable even if it is stored for 6 months at 40° C./75% RH.

Example 61

The preparation of the capsules containing the crystal forms of the present invention.

The formulation of capsules is shown in Table 3.

TABLE 3

| Capsule Formulation | |
|---|---|
| Ingredient | Content (mg/piece) |
| API (selected from the Known Crystal Form 1, the Known Crystal Form 2, Crystal Form VI of the present invention) | 71 |
| Microcrystalline cellulose (Avicel) | 60 |
| Sodium carboxymethyl starch (SSG) | 13 |

The steps to prepare the capsules are as follows:

1) Appropriately/according to the actual demand, separate the 0# hard capsules into a top and a bottom half, and mark/identify each half.

2) Place the bottom half into a capsule filling machine and make sure the filling funnel being on the top.

3) Blend API (selected from the Known Crystal Form 1, the Known Crystal Form 2 and Crystal Form VI of the present invention), microcrystalline cellulose (avicel) and sodium carboxymethyl starch (SSG) uniformly.

4) Make the above mixture into soft materials by using an appropriate amount of 50% aqueous ethanol solution, then screen to produce the wet granules.

5) Dry the wet granules, grind and disperse uniformly and then transfer them into the capsules.

6) Place the top half on the capsule, close the capsule until finally close tightly; then tap the capsules in order to blend/disperse the ingredients.

7) If the powder is near the top of the capsules at the beginning, slightly knock the capsule to settle down the powders.

8) Place such capsules in a small bottle marked appropriately (which should be large enough to move easily).

The XRPD test shows that, when the capsules use the Known Crystal Form 1 and the Known Crystal Form 2 as API and are prepared by the wet granulation process with water as the wetting agent, the crystal form in such capsules is unstable and has converted to Crystal Form VI of the present invention; when the capsules use Crystal Form VI of the present invention as API and are prepared by the wet granulation process with water as the wetting agent, the crystal form in such capsule is stable and still stable even if it is stored for 6 months at 40° C./75% RH.

Example 62

The preparation of the oral suspension containing the crystal forms of the present invention.

API (selected from Crystal Form VI of Dabrafenib of the present invention): 2 g;
  Cocklebur gum: 8 g;
  Sodium dihydrogen citrate: 2 g;
  Methylparaben: 1.4 g;
  Syrupus simplex: 150 mL;
  Orange flavor: 1 mL;
  Water: to 1,000 mL.

The steps to prepare the oral suspension are as follows:

Blend API (selected from Crystal Form VI of Dabrafenib of the present invention), cocklebur gum, sodium dihydrogen citrate, methylparaben, syrupus simplex and orange flavor, add water to 1,000 mL and stir the mixture uniformly. After that, divide the solution into 100 bottles with 20 mg API in each bottle.

The XRPD test shows that, the crystal form in the oral suspension in which the Known Crystal Form 1 and the Known Crystal Form 2 as API is unstable and has converted to Crystal Form VI of the present invention; Crystal Form VI of the present invention being as API in the oral suspension is stable and still stable even if it is stored for 6 months at 40° C./75% RH.

The scientists in this field may understand that, with the instructions of the present specification, some modifications or changes may be made on this Invention. These shall be made within the scope of this invention defined by the claims.

What is claimed is:

1. Crystal Hydrate Form VI of Dabrafenib with the structural formula shown below,

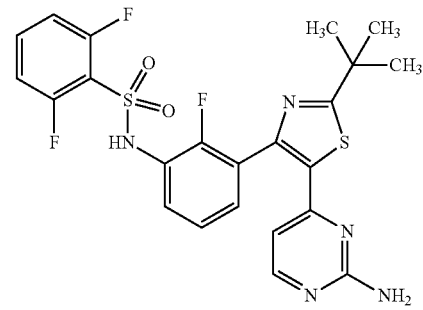 [SMILES: CC(C)(C)c1nc(-c2cccc(NS(=O)(=O)c3c(F)cccc3F)c2F)c(-c2ccnc(N)n2)s1]

characterized by a X-ray powder diffraction pattern measured using Cu—Kα radiation having the specific peaks at the diffraction angle 2θ of 10.4±0.2°, 17.6±0.2°, 21.6±0.2° and 25.1±0.2°.

2. The Crystal Hydrate Form VI of Dabrafenib according to claim 1, characterized by a X-ray powder diffraction pattern having the specific peaks at the diffraction angle 2θ of 10.4±0.2°, 11.2±0.2°, 13.1±0.2°, 13.3±0.2°, 16.7±0.2°, 17.6±0.2°, 18.3±0.2°, 21.2±0.2°, 21.6±0.2°, 25.1±0.2°, 25.8±0.2°, 27.6±0.2° and 31.8±0.2°.

3. The Crystal Hydrate Form VI of Dabrafenib according to claim 2, characterized by a X-ray powder diffraction pattern having the specific peaks at the diffraction angle 2θ of 8.1±0.2°, 10.4±0.2°, 11.2±0.2°, 13.1±0.2°, 13.3±0.2°, 14.4±0.2°, 16.2±0.2°, 16.7±0.2°, 17.6±0.2°, 18.3±0.2°, 21.2±0.2°, 21.6±0.2°, 25.1±0.2°, 25.8±0.2°, 26.3±0.2°, 26.8±0.2°, 27.6±0.2°, 31.1±0.2°, 31.8±0.2° and 32.9±0.2°.

4. The Crystal Hydrate Form VI of Dabrafenib according to claim 3, characterized by a X-ray powder diffraction pattern having the following specific peaks at the diffraction angle 2θ and their relative intensities:

| diffraction angle 2θ | relative intensity % |
|---|---|
| 8.1 ± 0.2° | 11.0 |
| 10.4 ± 0.2° | 40.5 |
| 11.2 ± 0.2° | 17.1 |
| 13.1 ± 0.2° | 13.2 |
| 13.3 ± 0.2° | 25.4 |
| 14.4 ± 0.2° | 10.2 |

-continued

| diffraction angle 2θ | relative intensity % |
|---|---|
| 16.2 ± 0.2° | 12.8 |
| 16.7 ± 0.2° | 27.6 |
| 17.6 ± 0.2° | 44.7 |
| 18.3 ± 0.2° | 13.3 |
| 21.2 ± 0.2° | 18.2 |
| 21.6 ± 0.2° | 100.0 |
| 25.1 ± 0.2° | 34.0 |
| 25.8 ± 0.2° | 16.6 |
| 26.3 ± 0.2° | 10.6 |
| 26.8 ± 0.2° | 10.0 |
| 27.6 ± 0.2° | 13.3 |
| 31.1 ± 0.2° | 12.3 |
| 31.8 ± 0.2° | 23.2 |
| 32.9 ± 0.2° | 10.3 |

5. A method of preparing the Crystal Hydrate Form VI of Dabrafenib according to claim 1 comprising:

(1) Putting a known crystal form or an amorphous form of Dabrafenib into a solvent system to form a suspension, stirring to crystallize, separating and drying the precipitated crystals to get Crystal Hydrate Form VI of Dabrafenib, wherein the solvent system is selected from water or a mixed solvent of water and an organic solvent, and wherein the organic solvent is selected from the group consisting of $C_1$~$C_4$ alcohols, $C_4$~$C_5$ esters, $C_2$~$C_5$ ethers, $C_3$~$C_4$ ketones, tetrahydrofuran, nitromethane, acetonitrile, $C_5$~$C_8$ alkanes and mixtures thereof; or (2) At room temperature, forming a solution of a known crystal form or an amorphous form of Dabrafenib in a mixed solvent of water and an organic solvent, placing the solution in a sealed atmosphere full of a diffusive solvent to crystallize, separating and drying the precipitated crystal to get Crystal Hydrate Form VI of Dabrafenib, wherein the organic solvent is nitromethane or isopropyl alcohol and wherein the diffusive solvent is a volatile ether; or (3) Adding water or a water-saturated $C_5$~$C_8$ alkane solution into a solution formed by a known crystal form or an amorphous form of Dabrafenib in an organic solvent, stirring to crystallize for 3~14 days, separating and drying the precipitated crystals to get Crystal Hydrate Form VI of Dabrafenib, wherein the organic solvent is selected from the group consisting of $C_1$~$C_4$ alcohols, $C_4$~$C_5$ esters, $C_2$~$C_5$ ethers, $C_3$~$C_4$ ketones, tetrahydrofuran, nitromethane, acetonitrile and mixtures thereof; or (4) Preparing a solution of a known crystal form or an amorphous form of Dabrafenib in a mixed solvent of water and an organic solvent at a temperature ranging from 40° C. to the boiling point of the mixed solvent, cooling and stirring the solution to crystallize, separating and drying the precipitated crystals to get Crystal Hydrate Form VI of Dabrafenib, wherein the organic solvent is selected from the group consisting of $C_1$~$C_4$ alcohols, $C_4$~$C_5$ esters, $C_2$~$C_5$ ethers, $C_3$~$C_4$ ketones, tetrahydrofuran, nitromethane, acetonitrile and mixtures thereof.

6. A pharmaceutical composition comprising a therapeutically effective amount of Crystal Hydrate Form VI of Dabrafenib for inhibiting one or more Raf-family kinases and at least a pharmaceutical acceptable excipient, wherein the Crystal Hydrate Form VI of Dabrafenib is characterized by a X-ray powder diffraction pattern measured using Cu—Kα radiation having the specific peaks at the diffraction angle 2θ of 10.4±0.2°, 17.6±0.2°, 21.6±0.2° and 25.1±0.2°.

7. The pharmaceutical composition according to claim 6, wherein the pharmaceutical composition is in a dosage form selected from the group consisting of tablets, capsules, suspensions, disintegrating tablets, immediate release tablets, slow release tablets and controlled release tablets.

8. A method for inhibiting one or more Raf-family kinases comprising administering to a mammalian subject an effective amount of the pharmaceutical composition according to claim 6.

9. The method according to claim 5, wherein in (1), the organic solvent is selected from the group consisting of methanol, ethanol, propanol, butanol, ethyl acetate, isopropyl acetate, ethyl ether, methyl tert-butyl ether, acetone, butanone, tetrahydrofuran, nitromethane, acetonitrile, methyl cyclohexane, n-heptane, n-hexane and cyclohexane.

10. The method according to claim 5, wherein in (1), the amount of the known crystal form or the amorphous form of Dabrafenib is between 1.1 and 20 times of its solubility in the solvent system at the operation temperature, the operation temperature is between room temperature to 60° C., and the duration of crystallization is between 3 and 14 days.

11. The method according to claim 5, wherein in (2), the volume content of water in the mixed solvent of water and the organic solvent is at least between 0.01% and 10%, and the diffusive solvent is mineral ether or isopropyl ether.

12. The method according to claim 5, wherein in (2), the solution concentration of the known crystal form or the amorphous form of Dabrafenib in the mixed solvent of water and the organic solvent is between 0.1 and 5 mg/mL, and the duration of crystallization is between 1 and 3 weeks.

13. The method according to claim 5, wherein in (3), the organic solvent is selected from the group consisting of methanol, ethanol, propanol, butanol, ethyl acetate, isopropyl acetate, ethyl ether, methyl tert-butyl ether, acetone, butanone, tetrahydrofuran, nitromethane, and acetonitrile, and the $C_5$~$C_8$ alkane is selected from the group consisting of cyclohexane, methyl cyclohexane, n-hexane, n-heptane and mixtures thereof, and the volume ratio of water or the water-saturated $C_5$~$C_8$ alkane solution to the organic solvent is between 0.1:1 and 100:1.

14. The method according to claim 5, wherein in (4), the organic solvent is selected from the group consisting of methanol, ethanol, propanol, butanol, ethyl acetate, isopropyl acetate, ethyl ether, methyl tert-butyl ether, acetone, butanone, tetrahydrofuran, nitromethane and acetonitrile, the volume content of water in the mixed solvent of water and the organic solvent is at least between 0.01% and 50%.

15. A method for inhibiting one or more Raf-family kinases comprising administering to a mammalian subject an effective amount of Crystal Hydrate Form VI of Dabrafenib according to claim 1.

* * * * *